United States Patent [19]
Kontos

[11] Patent Number: 6,077,279
[45] Date of Patent: Jun. 20, 2000

[54] DEVICE AND METHOD EMPLOYING ADHESIVE FOR SEALING BLOOD VESSELS AND THE LIKE

[75] Inventor: Stavros Kontos, Woodcliff Lake, N.J.

[73] Assignee: X-Site L.L.C., Totowa, N.J.

[21] Appl. No.: 09/075,383

[22] Filed: May 8, 1998

[51] Int. Cl.$^7$ ..................................................... A61B 17/00
[52] U.S. Cl. ............................................................ 606/148
[58] Field of Search .................................... 606/144, 148, 606/139, 212–214; 128/898, 899; 604/118, 121, 96, 98

[56] References Cited

U.S. PATENT DOCUMENTS

| | | | |
|---|---|---|---|
| 5,417,699 | 5/1995 | Klein et al. | 606/144 |
| 5,591,204 | 1/1997 | Janzen et al. | 606/213 |
| 5,725,551 | 3/1998 | Meyers et al. | 606/213 |
| 5,792,152 | 8/1998 | Klein et al. | 606/144 |

Primary Examiner—Michael Buiz
Assistant Examiner—Vikki Trinh
Attorney, Agent, or Firm—Kenyon & Kenyon

[57] ABSTRACT

A method and device for sealing an opening in an anatomical structure within a living body involves the introduction of a length of suture around the opening using a stitching device or known suturing techniques. The stitching device may be an elongated member having needle channels therethrough. After the stitching device is partially inserted in the anatomical structure, needles connected by a length of suture are pulled through the anatomical structure at opposite sides of the opening. The sealing device may be an elongated member with an adhesive channel and either a suture channel or a loop. After the suture has been separated from the stitching device, the ends of the suture are passed through the suture channel or loop. The suture is then pulled through the suture channel or loop to close the opening. After the opening has been closed, adhesive is passed through the adhesive channel and applied to the opening to seal the opening.

24 Claims, 20 Drawing Sheets

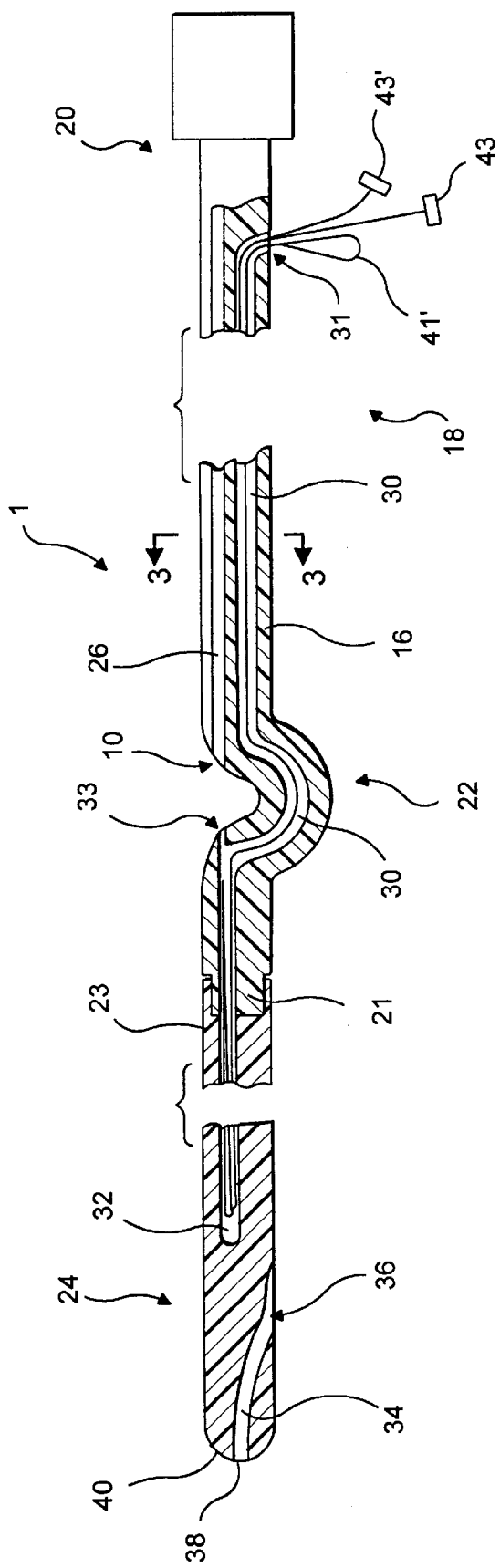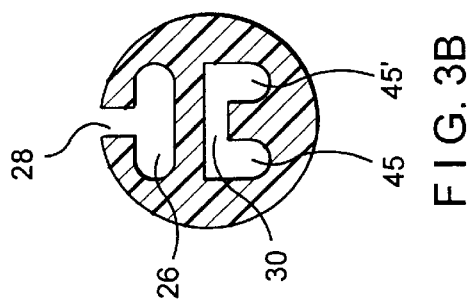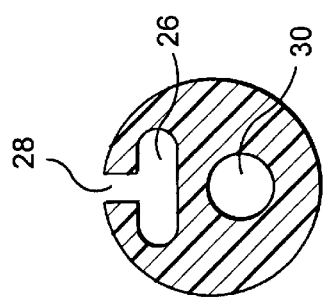

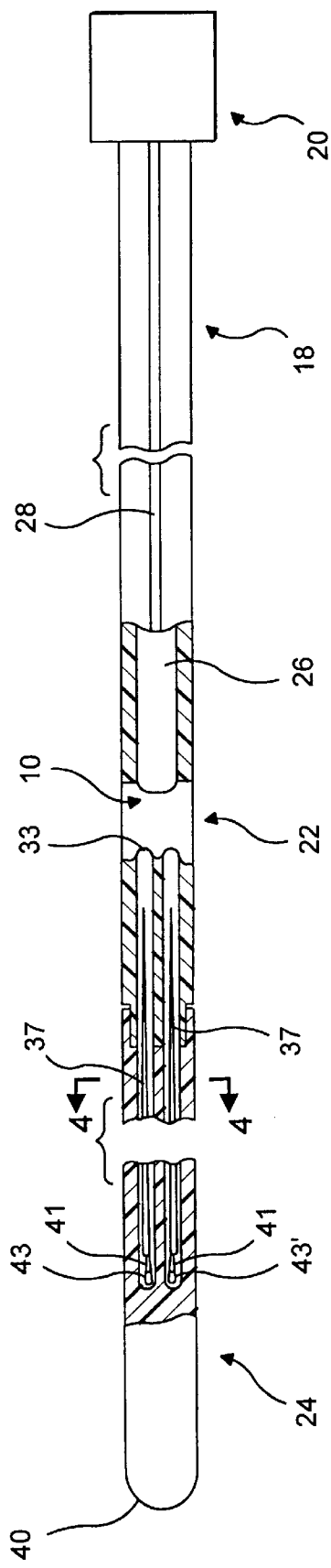
FIG. 2
FIG. 4A
FIG. 4B

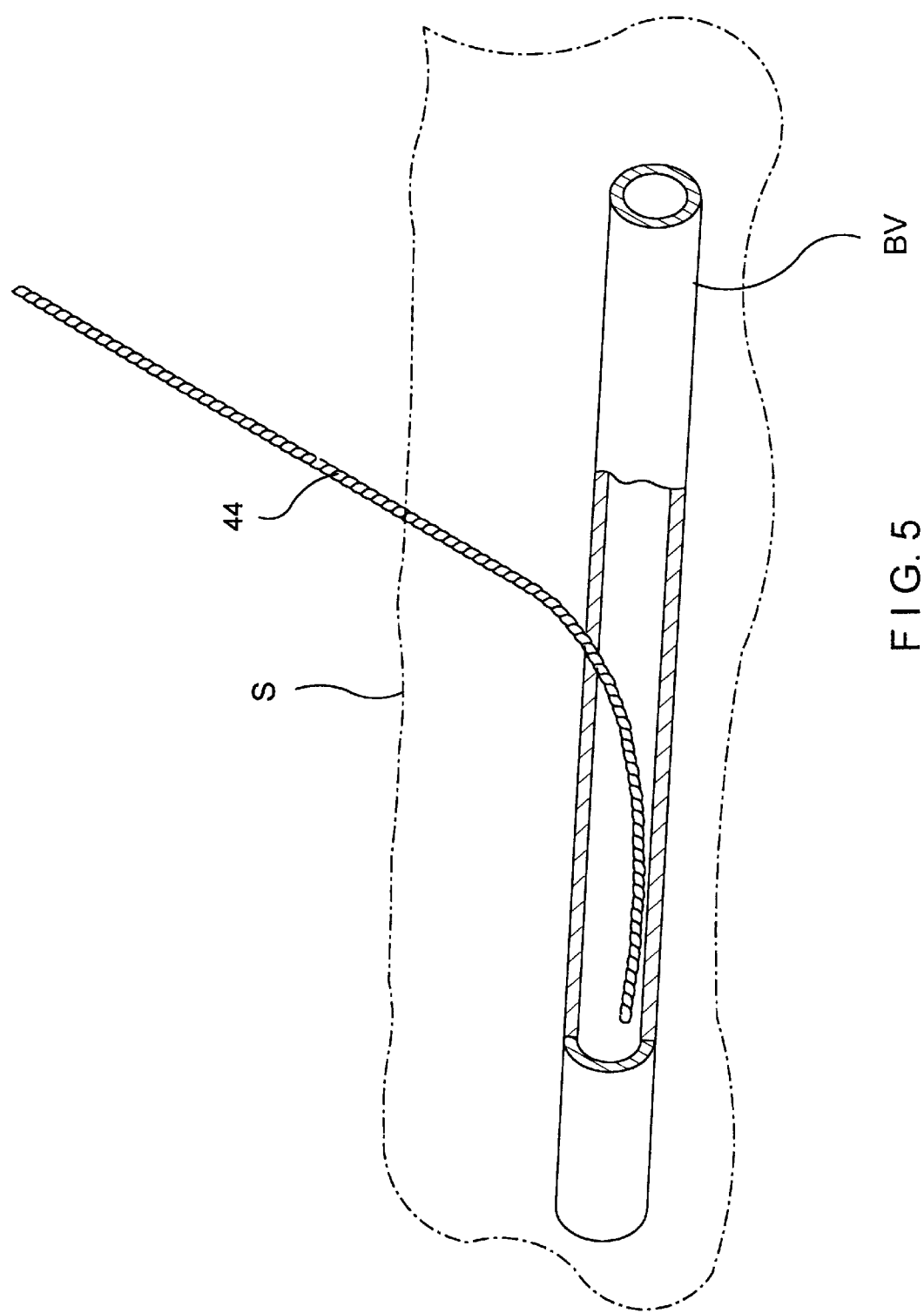

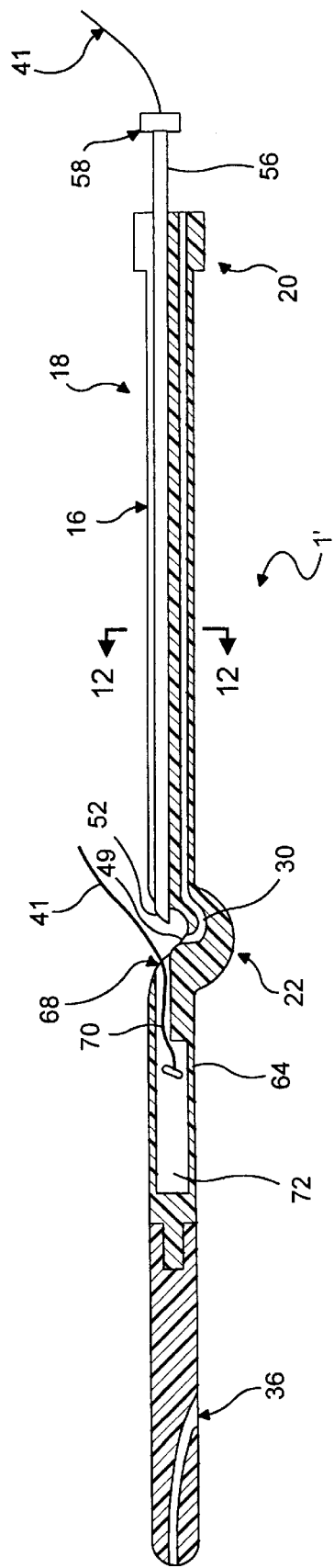
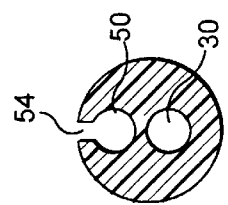
FIG. 11
FIG. 12

DEVICE AND METHOD EMPLOYING ADHESIVE FOR SEALING BLOOD VESSELS AND THE LIKE

FIELD OF THE INVENTION

The present invention relates generally to surgical instruments, and more specifically to a device and method employing adhesive for the sealing of punctures in blood vessels, internal organs and internal tissues accessed via a tissue tract.

BACKGROUND OF THE INVENTION

Many surgical procedures require the insertion of catheters and/or surgical devices into blood vessels and other internal structures. For example, in the treatment of vascular disease, it is often necessary to insert an instrument, i.e., a catheter, into the blood vessel to perform the treatment procedure. Such treatment procedures often involve piercing a wall of the blood vessel, inserting an introducer sheath into the blood vessel via the opening, and maneuvering the procedural catheter through the introducer sheath to a target location within the blood vessel. Of course in order to complete such a procedure, the sides of the opening in the wall of the blood vessel must be sealed to prevent bleeding while facilitating healing of the wound. At present, this sealing is commonly accomplished by application of direct pressure over the puncture site by a physician or other trained medical professional. Due to the dangers of thrombosis, the substantial reduction of blood flow through the blood vessel due to the application of pressure is undesirable and potentially dangerous to the patient. In addition, the procedure is extremely time consuming; often requiring that pressure be applied for forty-five minutes or more to achieve acceptable sealing.

Other sealing techniques include the application of a biogenic sealing material over the opening to seal the wound. However, with known methods the proper placement of the sealing material may be difficult to achieve. In addition, if the sealing material migrates to the interior of the blood vessel, the plug of sealing material may result in serious health risks to the patient.

As a result, devices have been developed which are inserted through the puncture in order to suture openings created in blood vessels. However, these devices suffer from various drawbacks.

For example, U.S. Pat. No. 5,417,699 to Klein et al. describes a device wherein two needles coupled to a distal end of an insertion shaft are surrounded by an outer sheath during insertion into an internal structure. Once inside the internal structure, the outer sheath is withdrawn and bowed sections of the needles, which had been constrained within the outer sheath against an outward spring bias, deploy away from the insertion shaft. The insertion shaft is then withdrawn drawing the needles through the walls of the internal structure. The arcuate shape of the needles is intended to bring the needles back along a curved path toward the insertion shaft so that the free ends of the needles may be captured on the shaft and the device withdrawn from the body. Thereafter, the distal ends of the needles must be detached from the insertion shaft so that a length of suture extending between distal ends of the two needles may be drawn through the walls of the internal structure to seal the opening.

However, the curved shape of the proximal ends of the needles of this device requires an insertion sheath of increased diameter. Thus, after withdrawal of a treatment catheter from an opening formed in an internal structure, insertion of the increased diameter outer sheath of the device of Klein et al. actually expands the opening in the wall of the internal structure. In addition, the device of Klein et al. employs several slidably mounted concentric shafts and mechanisms for the deployment and capture of the needles which make the device costly to manufacture and cumbersome to operate.

SUMMARY OF THE INVENTION

The present invention is directed to a system for sealing an opening in an anatomical structure within a living body. The system includes a stitching device and a sealing device. The stitching device may be any surgical stitching device adapted for suturing punctures in anatomical structures. One such device includes, for example, a flexible tube including a proximal portion extending along an axis coupled to a distal portion extending along the axis by a central portion, wherein the central portion extends away from the axis to form a gap between a distal end of the proximal portion and a proximal end of the distal portion. A needle retention channel formed within the distal portion for holding a plurality of needles therein extends along the axis to an opening formed in the proximal end of the distal portion. In addition, a needle receiving channel formed within the proximal portion extends along the axis to an opening formed in the distal end of the proximal portion. Finally, a lumen extends from an opening formed in the end of the proximal portion to the needle retention channel. Thus, when the stitching device is in an operative position, the flexible tube extends through the opening in the anatomical structure with the opening in the distal end of the proximal portion and the opening in the proximal portion on opposite sides of the anatomical structure.

The sealing device may also include an elongated tube having a suture channel and an adhesive channel. The suture channel is adapted to receive a suture therethrough, and sized so that when the suture is drawn through the suture channel, the puncture is pulled shut. The adhesive channel is adapted for connection to an adhesive source, and includes an opening for distribution of adhesive.

The present invention is also directed to a method including the steps of guiding a stitching device into an opening in an anatomical structure, suturing the anatomical structure, detaching one or more sutures from the stitching device, drawing the sutures through a sealing device to pull the opening shut, and applying adhesive through the sealing device to seal the opening. The stitching device may include substantially linear proximal and distal portions extending along a common axis and a curved central portion coupling the proximal and distal portions so that a gap is formed therebetween. The step of suturing the anatomical structure may include, for example, the following steps: positioning the suturing device so that the curved central portion is within the opening with a needle retention channel opening on a distal side of the anatomical structure and a needle receiving channel opening on a proximal side of the anatomical structure; drawing a pull cord attached to a distal end of a first needle out to bring a first needle proximally out of the needle retention channel through the anatomical structure and through the needle receiving channel to bring a first end of the suture through the anatomical structure; and, thereafter, rotating the stitching device to a second desired position so that a second portion of the anatomical structure adjacent to the opening is located within the gap and drawing a pull cord attached to a distal end of a second needle to bring the second needle proximally out of the needle retention channel through the anatomical structure and into the needle receiving channel so that the second end of the suture is drawn through the anatomical structure.

A second stitching device according to the present invention comprises a flexible tube including proximal and distal portions and a curved central portion coupling the proximal and distal portions so that a gap is formed therebetween. A puncture needle channel extends through the proximal portion to an opening formed in the distal end of the proximal portion, while a puncture needle receiving channel extends through the distal portion to a suture retention channel of relatively larger cross-sectional area. A puncture needle including a central lumen is slidably received in the puncture needle channel so that, by applying pressure to a proximal end of the puncture needle, a user may manually move the puncture needle out of the opening formed in the distal end of the puncture needle channel, across the gap and into the puncture needle retention channel until a distal end of the puncture needle is received within the suture retention chamber. A piston is slidably received in the central lumen so that, when the distal end of the puncture needle is received within the suture retention chamber, a user may move the piston distally through the central lumen to release the contents of the central lumen into the suture retention chamber.

BRIEF DESCRIPTION OF THE DRAWINGS

FIG. 1 shows a side view of a cross-section of a suturing device according to a first embodiment of the invention;

FIG. 2 shows a top view of a cross-section of a suturing device according to the first embodiment of the invention;

FIG. 3A shows a cross-section of a device according to the first embodiment of the invention taken along line 3—3 of FIG. 1;

FIG. 3B shows an alternative cross-section of a device according to the first embodiment of the invention taken along line 3—3 of FIG. 1;

FIG. 4A shows a cross-section of a device according to the first embodiment of the invention taken along line 4—4 of FIG. 2;

FIG. 4B shows an alternative cross-section of a device according to the first embodiment of the invention taken along line 4—4 of FIG. 2;

FIG. 5 shows a partially cross-sectional view of a blood vessel within a body with a guide wire inserted therein;

FIG. 11 shows a side view of a cross-section of a suturing device according to a second embodiment of the invention;

FIG. 12 shows a cross-section of a device according to the second embodiment of the invention taken along line 12—12 of FIG. 11;

DETAILED DESCRIPTION OF THE INVENTION

Figure 6A:
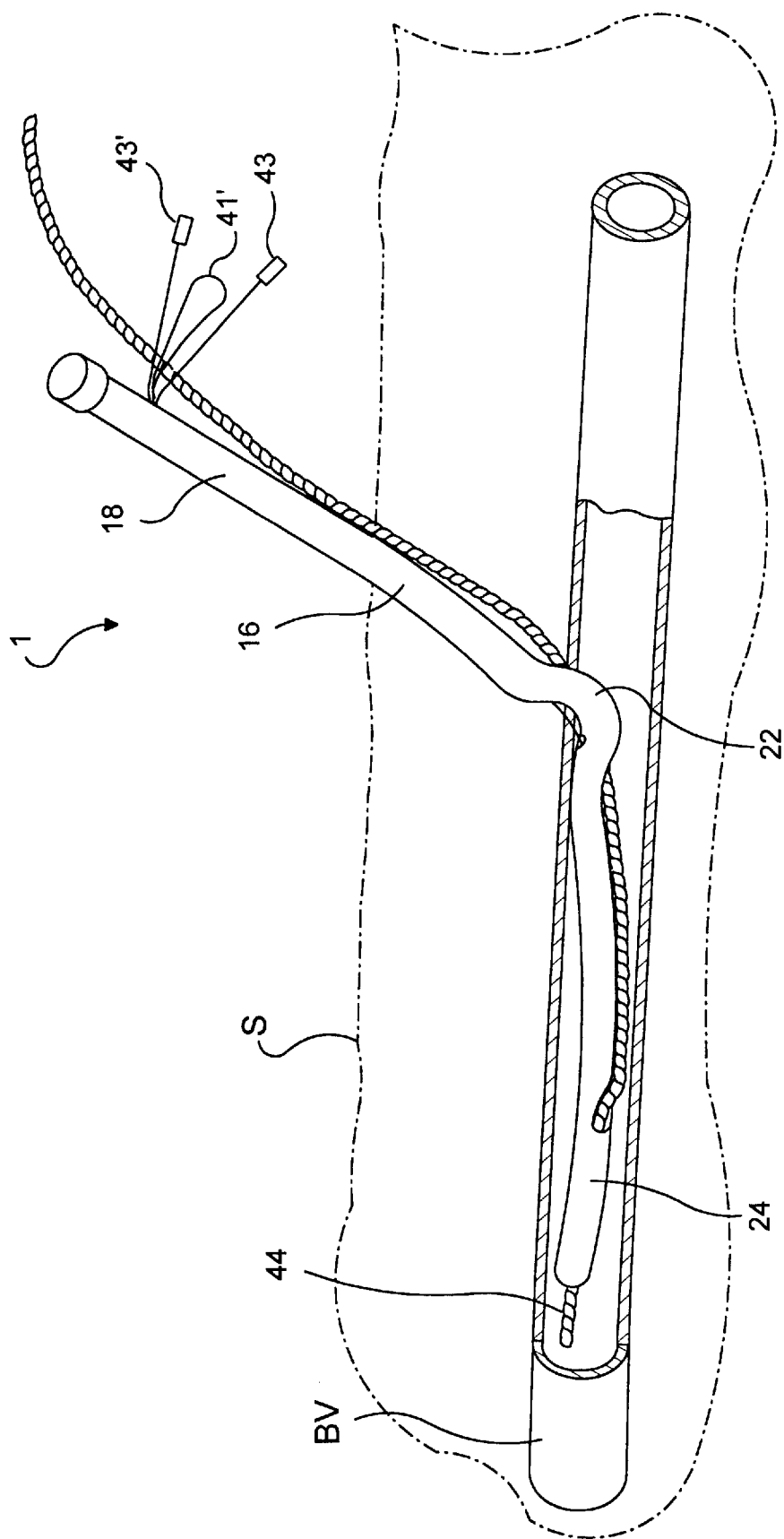
FIG. 6A shows a partially cross-sectional view of the blood vessel with a device according to the first embodiment of the present invention received on the guide wire in a first desired position.

Referring now to the drawings, in which like reference numerals identify similar or identical elements, FIGS. 1–8 show a device 1 according to a first embodiment of the invention for suturing punctures in blood vessels, internal organs and the like. The device 1 includes flexible tube 16 of substantially circular cross-section, which has a proximal part 18 and a distal part 24. The proximal part 18 extends from a first end 20 through a central arcuate portion 22 to a second end 21 which mates with a proximal end 23 of the distal part 24. The central arcuate portion may preferably be substantially circular with a radius of from 0.100" to 0.600". The flexible tube 16 is preferably constructed of a thermoplastic such as polyurethane, polyethylene, or the like, in two or three parts bonded together. The various parts of the flexible tube 16 may preferably be either extruded or molded. Those skilled in the art will recognize that it will be more economical to extrude the parts including one or two lumens, while the more complex, and curved sections of the flexible tube 16 may be molded. The length of the flexible tube may be selected to fit the requirements of a particular situation and is preferably between 1" and 16" in length.

The flexible tube 16 includes a large interior needle withdrawal lumen 26 which extends through the proximal part 18 from the first end 20 to an opening 10 at a proximal end of the central arcuate portion 22. As seen in FIGS. 3A and 3B, the needle withdrawal lumen 26 may preferably be oval in cross-section and may include an optional slot 28 opening to the outside of the flexible tube 16.

In addition, a flash back lumen 30 extends from an opening 31 formed in the proximal part 18 through the central arcuate portion 22 to open into two needle retention bores 32 and 32' formed side-by-side in the distal part 24. As seen in FIG. 3A, the flash back lumen 30 may be circular in cross-section and is sized to simultaneously accommodate two strands of the suture 41 and the two pull cords 43 and 43'. However, as shown in FIG. 3B, the cross-section of the flash back lumen 30 may preferably include side-by-side hemispherical channels 45 and 45' for receiving the loop 41' of the suture 41 and the two pull cords 43 and 43'. This helps to ensure that the second needle 37 is not accidentally drawn out of the needle retention bore 32' when the first 37 is being pulled out. The needle retention bores 32 and 32' extend from distal ends to openings 33 and 33', respectively, formed at a position in the distal end of the central arcuate portion 22 opposite the opening 10. In addition, a substantially straight stiffening member may be inserted into the flash back lumen 30 in order to straighten the central arcuate portion 22 during insertion of the device 1 into the body. Alternatively, the device 1 may be made straight and, after insertion into the body, a curved stiffening member may be inserted to bend the device 1 thereby creating the central arcuate portion 22.

As seen in FIGS. 4A and 4B, the retention bores 32 and 32' have cross-sectional shapes including first portions 35, each shaped to receive a needle 37 and second portions 39, each shaped to receive a suture 41 and pull cord 43 or 43'. The first portions 35 are shaped to correspond to the cross-section of the needles 37 which in the preferred embodiment is substantially circular. The second portions 39, which are of reduced size so that the needles 37 are unable to enter, may be either rectangular or triangular projections extending from the first portions 35 and are sufficiently large to simultaneously accommodate the suture 41 and one of the pull cords 43 and 43'. The suture 41, which will preferably be in the range of 0.004" to 0.010" in diameter and from 15" to 35" in length, may be formed of either "reabsorbable" or "non-reabsorbable" material, as is well known in the art. The pull cords 43 and 43' will preferably be formed of non-reabsorbable material and will be of similar diameter to the suture 41. Those skilled in the art will recognize that the function of the pull cords 43 and 43' may be filled by a loop 41' of the suture 41 coupled between the distal ends of the needles 37 extended through the flash back lumen 30 so that, when the loop 41' of the suture 41 is extended proximally, the needles 37 are urged proximally through the needle retention bores 32 and 32'.

As the device 1 according to the first embodiment includes a single pair of needles, this device should preferably be used to close punctures of 9.0 French size and smaller (each French size representing 0.13" in diameter). The flexible tube 16 will, therefore, preferably be 6.0 or 8.0 French size. As described below in reference to further embodiments of the invention, devices employing two or more pairs of needles 37 may be employed to close punctures larger than 9.0 French size. Each of the needles 37 may preferably be constructed of stainless steel, be between 2" and 8" in length and have a diameter between 0.010" and 0.030".

When the device 1 is in an operative configuration, the suture 41 extends between the distal ends of two needles 37 received in the needle retention bores 32 and 32'. In the first embodiment of the invention, optional pull cords 43, 43' extend from the distal end of each of the needles 37 through the second portions 39 of the needle retention bores 32 and 32', via the flash back lumen 30, to the opening 31. However, the suture 41 may, alternatively, extend from the distal ends of the needles 37 through the second portions 39 of the needle retention bores 32 and 32', via the flash back lumen 30, to the opening 31 so that a portion of the suture loop 41' which extends out from the opening 31 may provide the function of the pull cords 43 and 43', as described below.

Finally, a guide wire lumen 34 extends through the distal part 24 of the device 1 from a proximal opening 36 to a distal opening 38 formed in a second end 40 of the device 1.

In operation, as shown in FIGS. 5–10, when an invasive procedure is performed on a patient which requires the insertion of a catheter into a blood vessel (or other structure within the body), an introducer sheath is inserted through the skin (S) into the patient's body through a puncture (P) in a wall of the blood vessel (BV). A guide wire 44 is inserted through the puncture to a target area within the blood vessel and a catheter is inserted through the introducer sheath, along the guide wire 44, to a target area within the blood vessel. After the procedure is complete, the catheter and the introducer sheath are withdrawn and the guide wire 44 is left in place. A proximal end of the guide wire 44 is then inserted through the guide wire lumen 34 and the device 1 is inserted into the body and moved along the guide wire 44 through the puncture until the central arcuate portion 22 straddles a portion of the blood vessel wall adjacent to the puncture.

By observing the flash back lumen 30 and the needle withdrawal lumen 26, the doctor may determine when the device 1 is in the desired position. Specifically, when the device 1 is inserted far enough into the blood vessel, blood will be observed in the flash back lumen 30. However, if blood is observed in the needle withdrawal lumen 26, the doctor knows that the device 1 has been inserted too far into the blood vessel.

As the device 1 is inserted into the blood vessel, the flexible tube 16 bends so that the device 1 is received within, and extends in the direction of the blood vessel without straining the vessel. In this position, the openings 33 and 33' are on the distal side of the puncture facing the opening 10 which is located on the proximal side of the puncture.

Figure 6B:
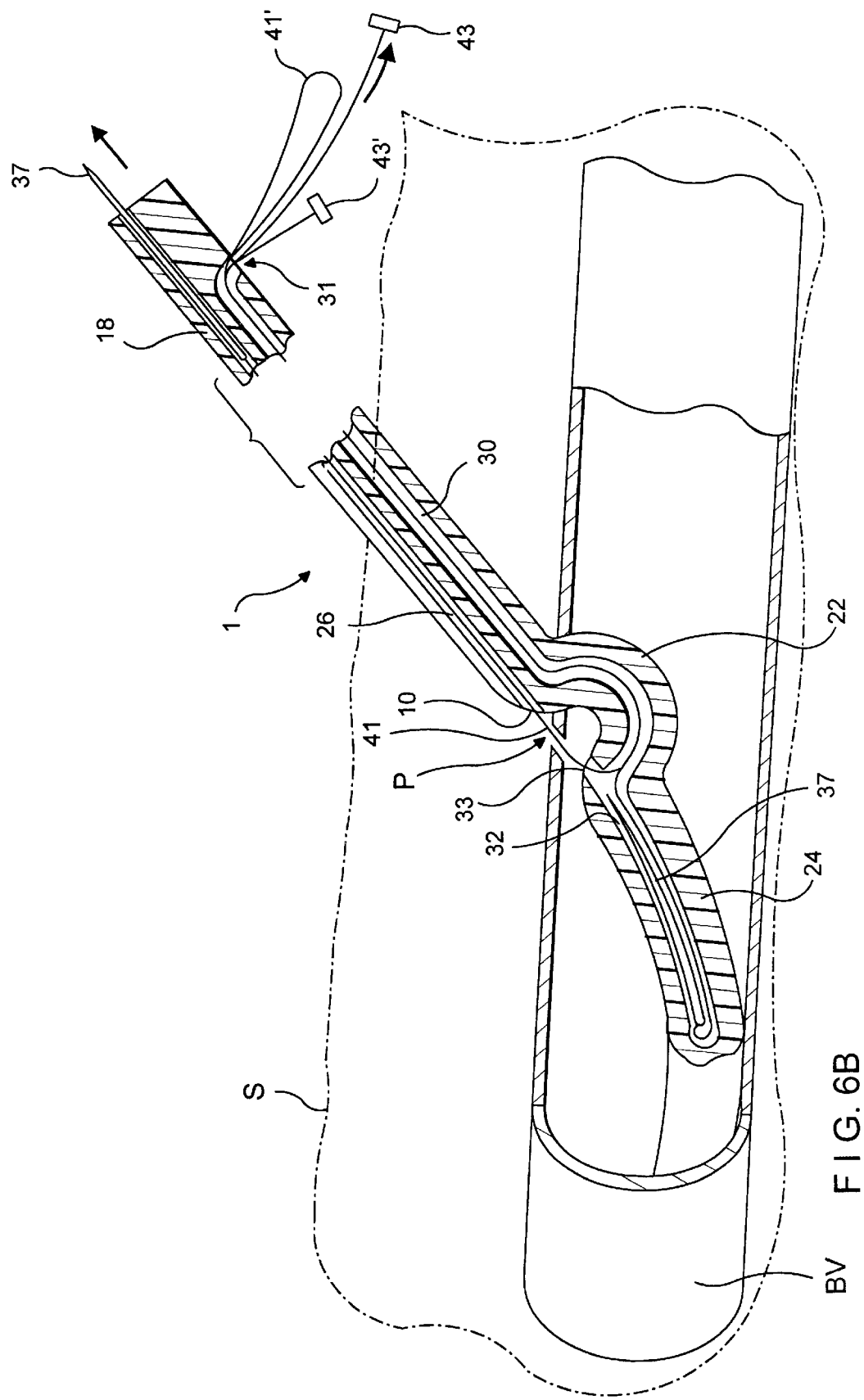
FIG. 6B shows a partially cross-sectional view of the blood vessel with the device as shown in FIG. 6A wherein a needle has been drawn through the body tissue received in the central gap.

As shown in FIG. 6B, the doctor then rotates the device 1 into a desired orientation and draws the pull cord 43 out of the opening 31, thus drawing one of the needles 37 forward through the needle retention bore 32 so that a pointed, proximal end of the needle 37 is drawn through the wall of the blood vessel, enters the opening 10 and extends into the needle withdrawal lumen 26. The needle 37 is then withdrawn through the needle withdrawal lumen 26, drawing a first end of the suture 41 through the wall of the blood vessel and into the needle withdrawal lumen 26. The needle 37 is drawn forward by means of the pull cord 43 until a proximal end of the needle 37 protrudes from the proximal end of the needle withdrawal lumen 26. The proximal end of the needle 37 is then grasped by the doctor and withdrawn from the needle withdrawal lumen 26. In order to ensure that the needles 37 will extend through the needle withdrawal lumen 26, the needles 37 will preferably be at least 4" in length.

Figure 7:
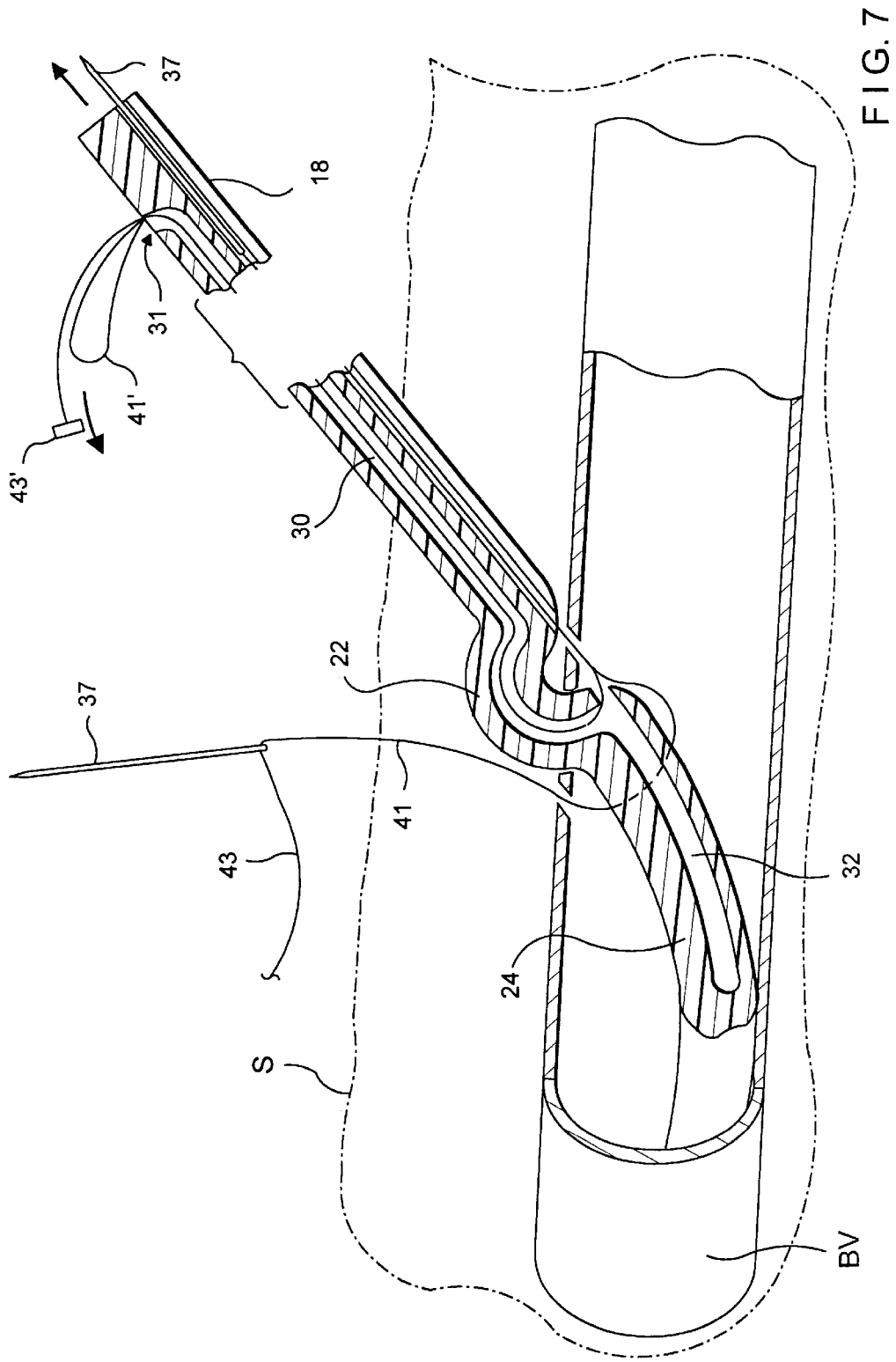
FIG. 7 shows a partially cross-sectional view of the blood vessel with a device according to the first embodiment of the present invention in a second desired position.

Thereafter, the doctor rotates the device 1, as shown in FIG. 7, until the central arcuate portion 22 straddles the blood vessel wall in a desired position relative to the point at which the first end of the suture 41 penetrated the blood vessel wall. Those skilled in the art will understand that this "desired position" will usually be on the opposite side of the puncture, so that the device 1 will be rotated approximately 180° after the first needle 37 is withdrawn. When the device 1 is in the second desired orientation, the doctor draws the pull cord 43' out of the opening 31 thereby urging the second needle 37 forward through the needle retention bore 32' so that the pointed, proximal end of the second needle 37 is drawn through the wall of the blood vessel, enters the opening 10 and extends into the needle withdrawal lumen 26. The second needle 37 is withdrawn through the needle withdrawal lumen 26, drawing the second end of the suture 41 through the wall of the blood vessel and into the needle withdrawal lumen 26 as described above.

Figure 8:
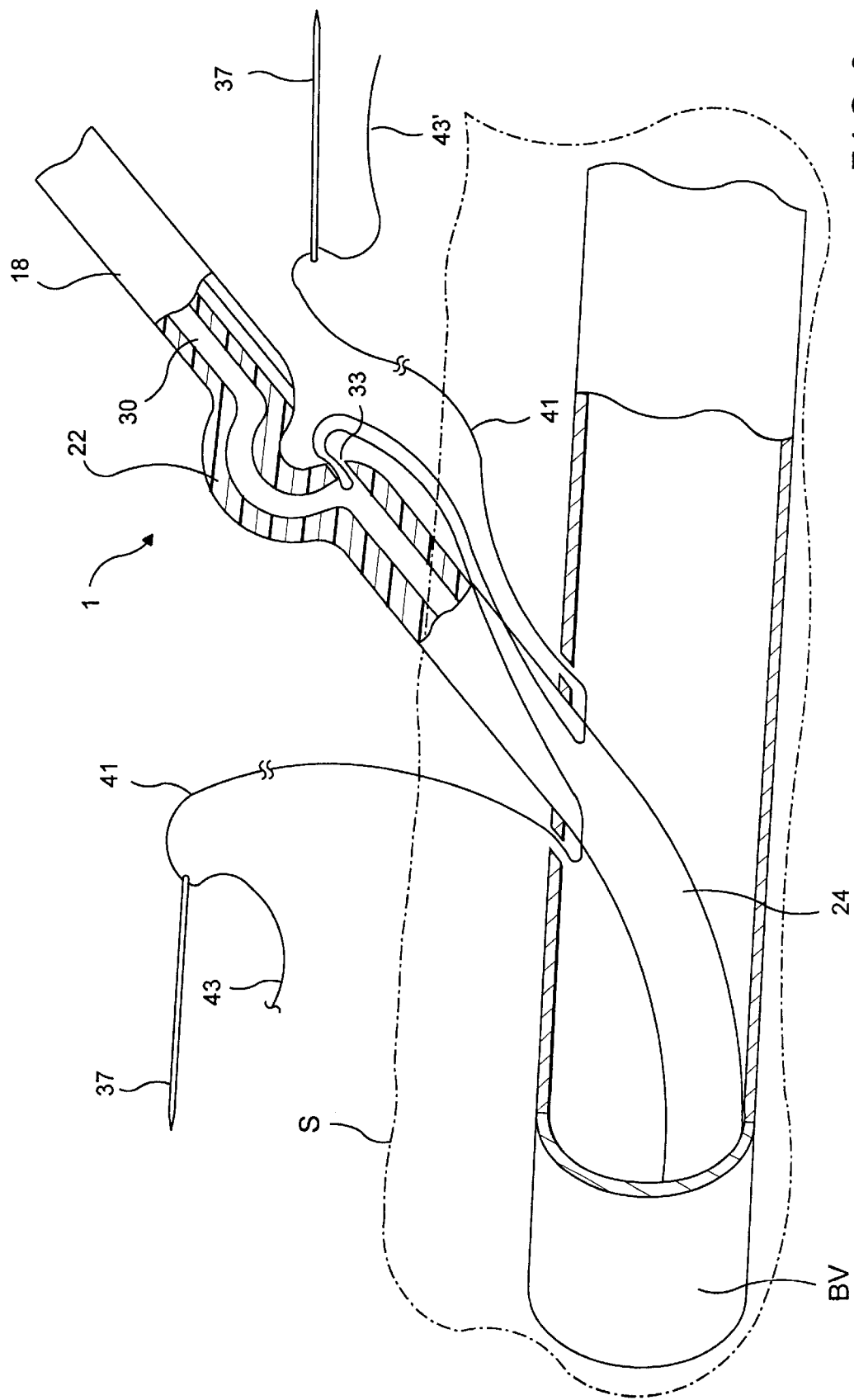
FIG. 8 shows a partially cross-sectional view of the blood vessel with a device according to the first embodiment of the present invention partially removed from the blood vessel.
Figure 9:
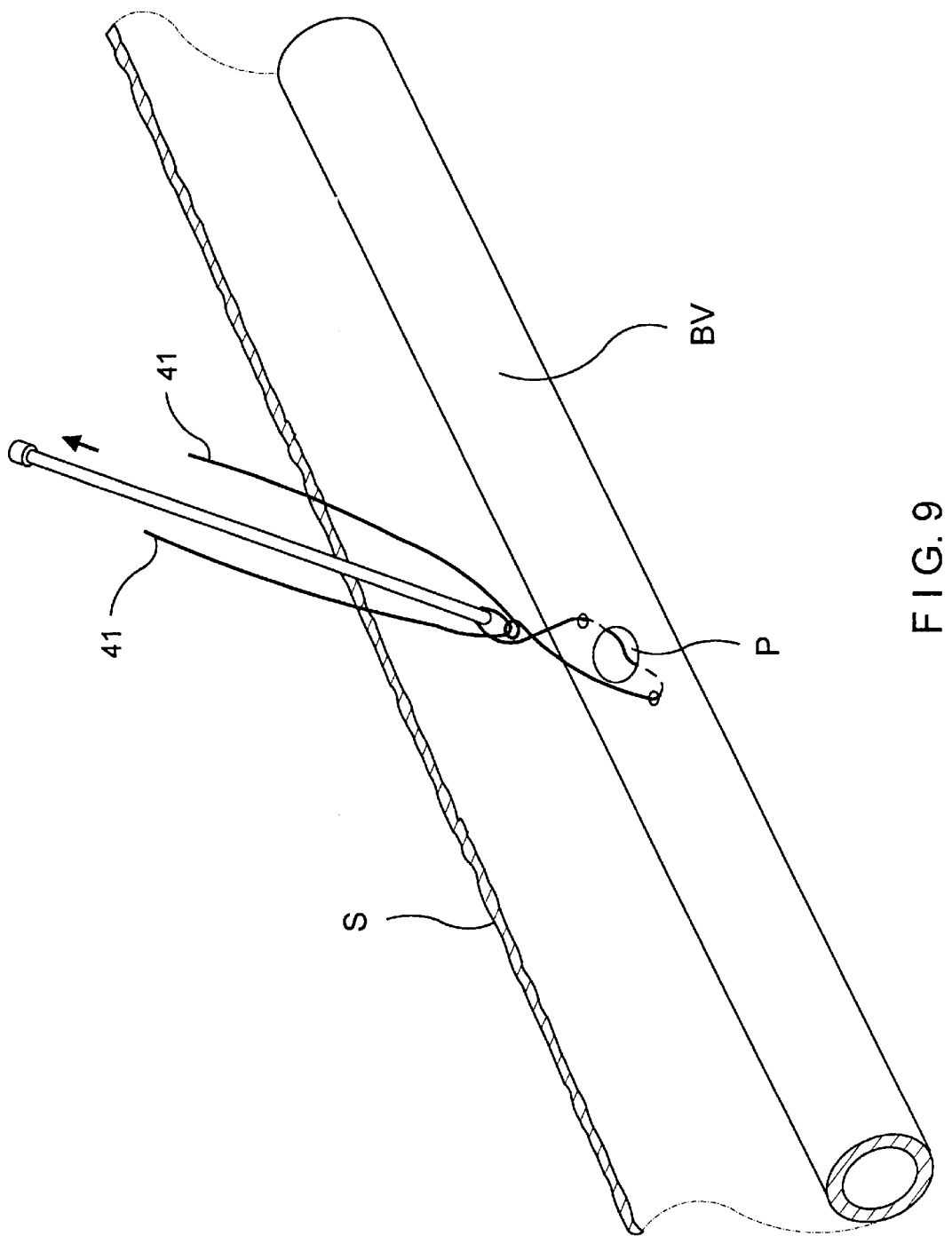
FIG. 9 shows a slip knot tied in a suture loop extending through the wall of the blood vessel being urged toward the blood vessel.
Figure 10:
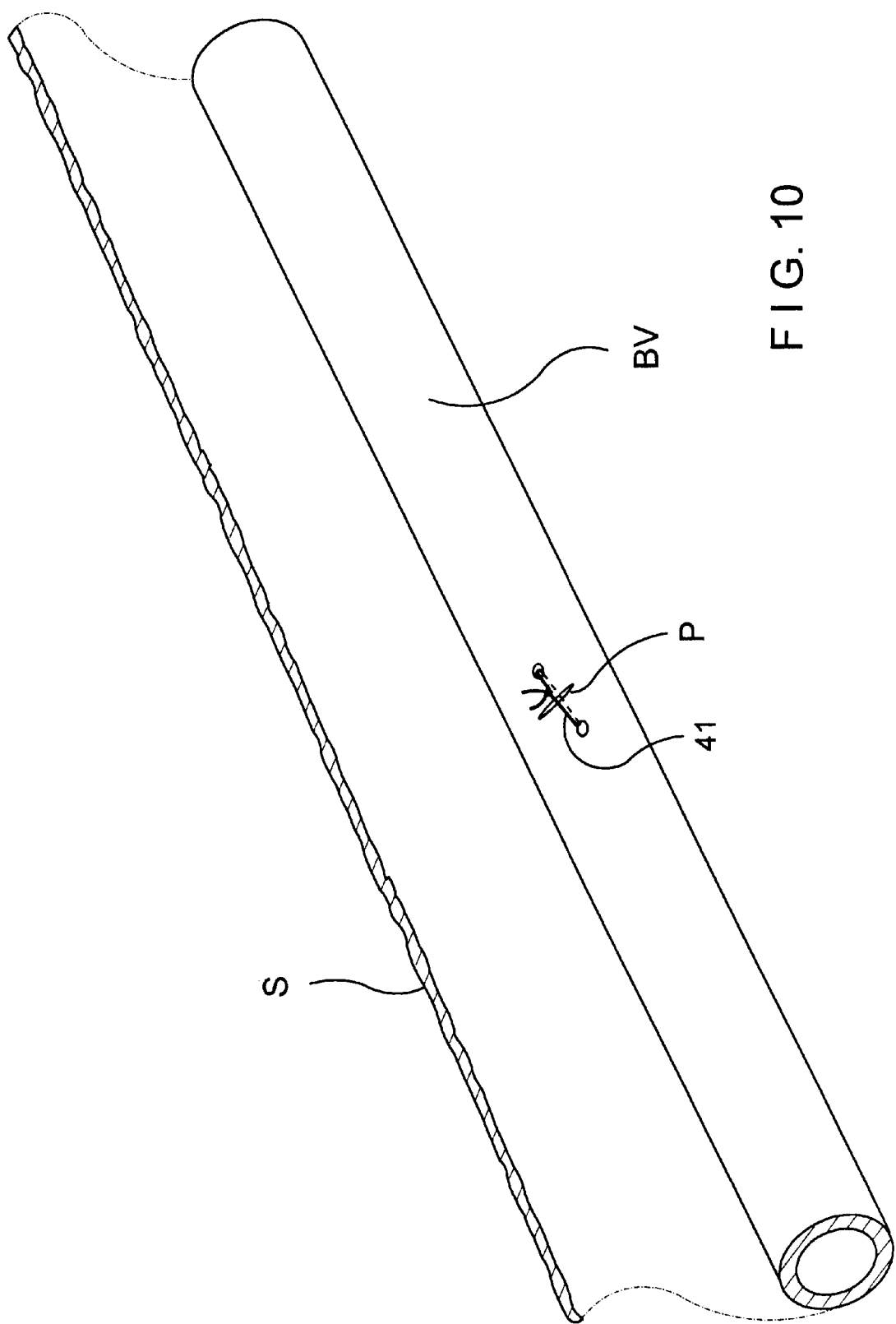
FIG. 10 shows a suture sealing the puncture.
Figure 13:
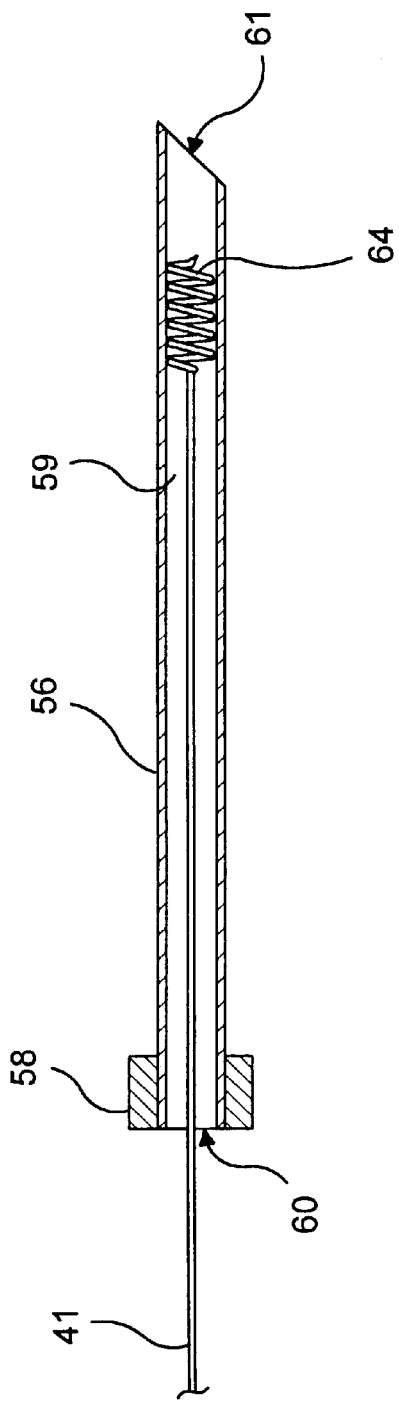
FIG. 13 shows a cross-sectional view of a puncture needle according to the second embodiment of the present invention.
Figure 14:
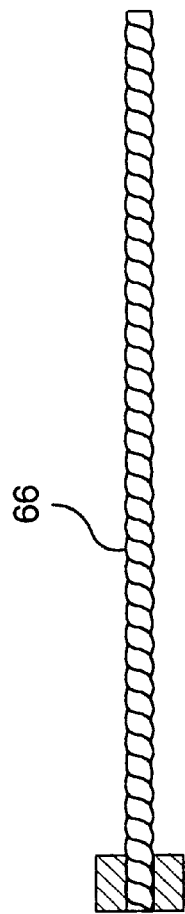
FIG. 14 shows a side view of a plunger according to the second embodiment of the present invention.
Figure 15:
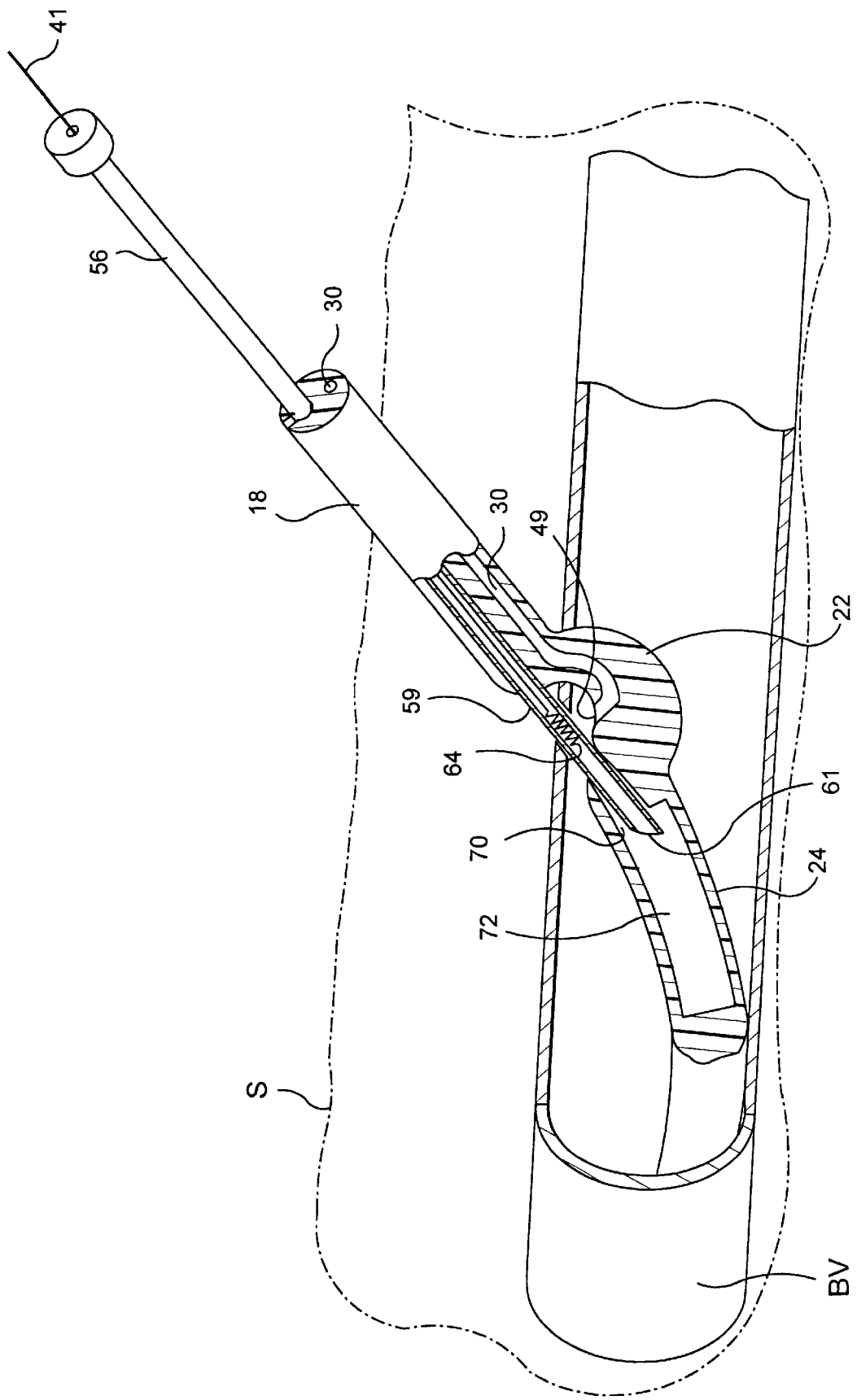
FIG. 15 shows a partially cross-sectional view of the blood vessel with a device according to the second embodiment of the present invention in a first desired position.
Figure 16:
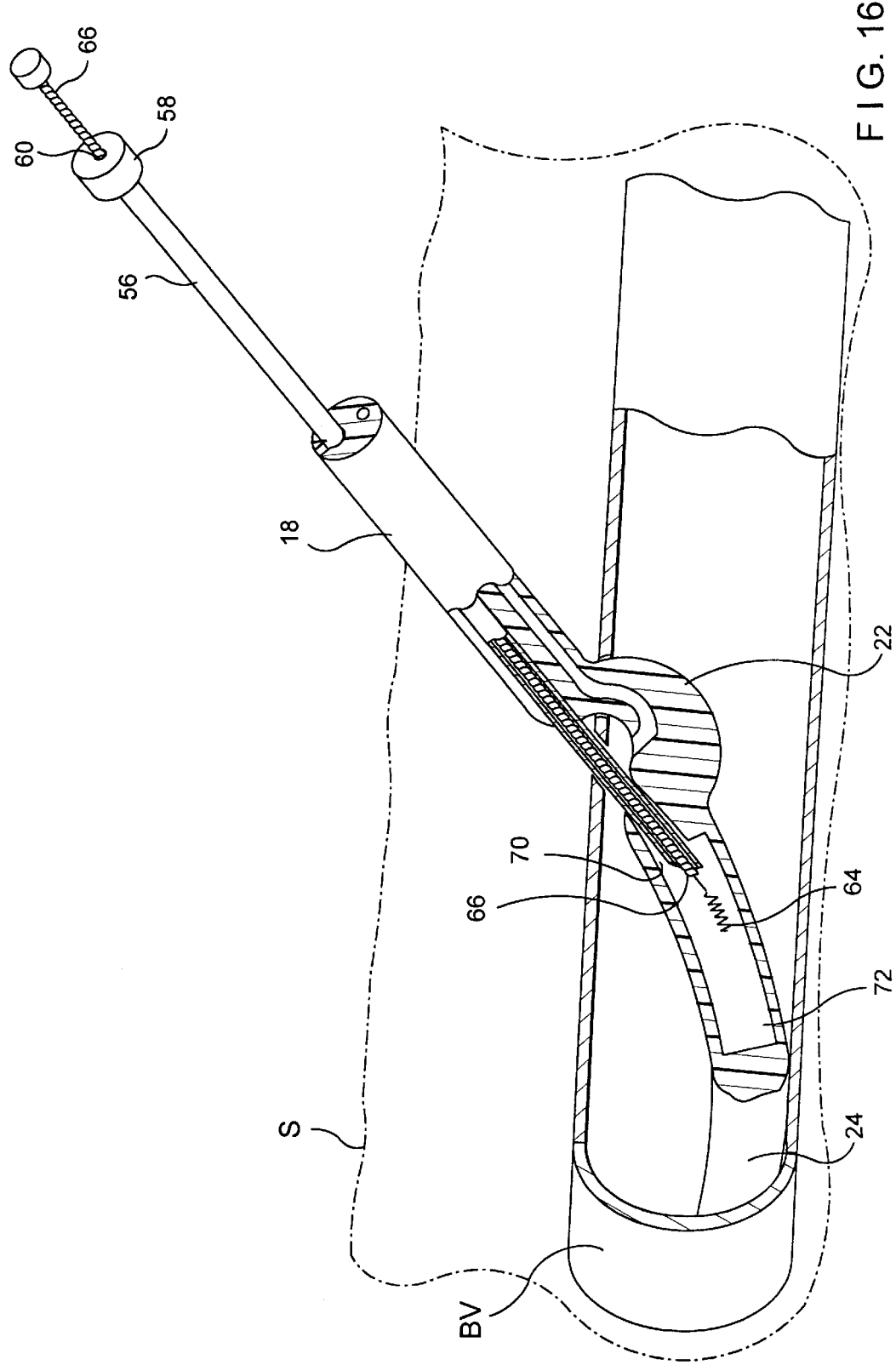
FIG. 16 shows a partially cross-sectional view of the blood vessel with a device according to the second embodiment of the present invention in the first desired position where a suture has been passed through the wall of the blood vessel and introduced into a suture retention chamber.

As shown in FIGS. 8–10, the doctor withdraws the device 1 from the body and detaches the suture 41 from the ends of the needles 37 and ties the two ends together in a slip knot which is urged inward toward the blood vessel and drawn tight in order to seal the puncture. Of course, those skilled in the art will appreciate that, once the two ends of the suture 41 have been drawn through the blood vessel wall, various other methods of fastening the two ends together may be employed.

FIGS. 11–19 show a suturing device according to a second embodiment of the present invention. The flexible tube 16 of the device 1' according to the second embodiment is preferably similar in size and flexibility to the device 1 of the first embodiment and differs only as described below. In addition, those skilled in the art will recognize that, except where specifically stated, each of the variations described above in reference to the first embodiment may also be applied to all other embodiments.

As seen in FIG. 12, the cross-section of the proximal part 18 of the device 1' shows a flash back lumen 30 of circular cross-section. The flash back lumen 30 of this embodiment extends from the first end 20, through the proximal part 18 to an opening 49 formed adjacent to the opening 68.

In addition, instead of the needle withdrawal lumen 26 of the first embodiment, the proximal part 18 of the device 1' includes a substantially circular puncture needle channel 50 extending from the first end 20 of the device 1' to an opening 52 at a proximal end of the central arcuate portion 22. This puncture needle channel 50 is also shown including an optional slot 54 extending through the surface of the flexible tube 16 along the length of the puncture needle channel 50.

A puncture needle 56, having an increased diameter gripping surface 58 at a proximal end, is slidably received in the puncture needle channel 50. The puncture needle 56 includes a central channel 59 extending from an opening 60 formed in the gripping surface 58 to an opening 61 formed in a distal end 62 of the puncture needle 50. One suture 41, integrally formed with or coupled to a respective anchor member 64, is received within the central channel 59. The anchor member 64 may be constructed as a coiled stainless steel spring.

Those skilled in the art will recognize that, if the puncture needle 56 is provided with a slot extending from a proximal end to a distal end thereof, a suture loop 41' may be formed with a single suture 41 having anchor members 64 at both ends. That is, after a first end of the suture has been inserted into the suture retention chamber 72, a first length of this suture 41 may be drawn out through the slot and a second anchor member 64 attached to a second end of the suture 41 may be inserted into the suture retention chamber 72 through a second portion of the blood vessel wall as described above. Thereafter, the device 1' is withdrawn from the body and the two ends of the suture loop 41' are tied together and, using known techniques, the knot is maneuvered so that it ends up on the outside of the blood vessel.

A plunger 66 is slidably received within the central channel 59 so that the anchor member 64 is located between the opening 61 and a distal end of the plunger 66 so that, when the plunger 66 is urged distally into the central channel 59, the anchor member 64 is moved toward the opening 61.

An opening 68 opposite the opening 52 at a distal end of the central arcuate portion 22, extends through a needle reception slot 70 to a suture retention chamber 72 which has an increased diameter relative to the needle reception slot 70. Those skilled in the art will recognize that many variations may be made to the structure of the anchor member 64 so long as sufficient stiffness is maintained and the anchor member is dimensioned so as to prevent the suture 41 from being withdrawn from the suture retention chamber 72 during withdrawal of the device 1' from the body.

In operation as shown in FIGS. 15–19, the device 1' is positioned with the central arcuate portion 22 straddling the blood vessel wall with the openings 52 and 68 on opposite sides of the wall (proximal and distal, respectively) and rotated to a desired position as described above in regard to the device 1 of the first embodiment.

As described above in regard to the device 1, the flash back lumen 30 may be used to determine whether or not the device 1' is in the desired position. Specifically, when the device 1' is in the desired position, blood should be observed only in the flash back lumen 30, not in the needle channel 50. Blood in the needle channel 50 indicates that the device 1' has been advanced too far into the blood vessel. That is, blood in the needle channel 50 indicates that the opening 52 is improperly positioned within the blood vessel. When the device 1' is properly positioned, the doctor presses upon the gripping surface 58 to urge the a sharp, distal end of the puncture needle 56 distally out of the opening 52, through the wall of the blood vessel and into the opening 56.

When the puncture needle 56 has been inserted into the suture retention chamber 72, the doctor pushes the plunger 66 distally within the central channel 59 to release the anchor member 64 into the suture retention chamber 72. The puncture needle 56 is then withdrawn from the suture retention chamber 72 and the plunger 66 is completely withdrawn from the central channel 59.

Where the device 1' includes the optional slot 54, the suture 41 may then be withdrawn from the puncture needle channel 50 through the slot 54. This allows the diameter of the puncture needle channel 50 to be minimized while providing sufficient room for the puncture needle 56 to pass therethrough. Then a second anchor member 64 and a second suture 41 are inserted into the central channel 59.

Figure 17:
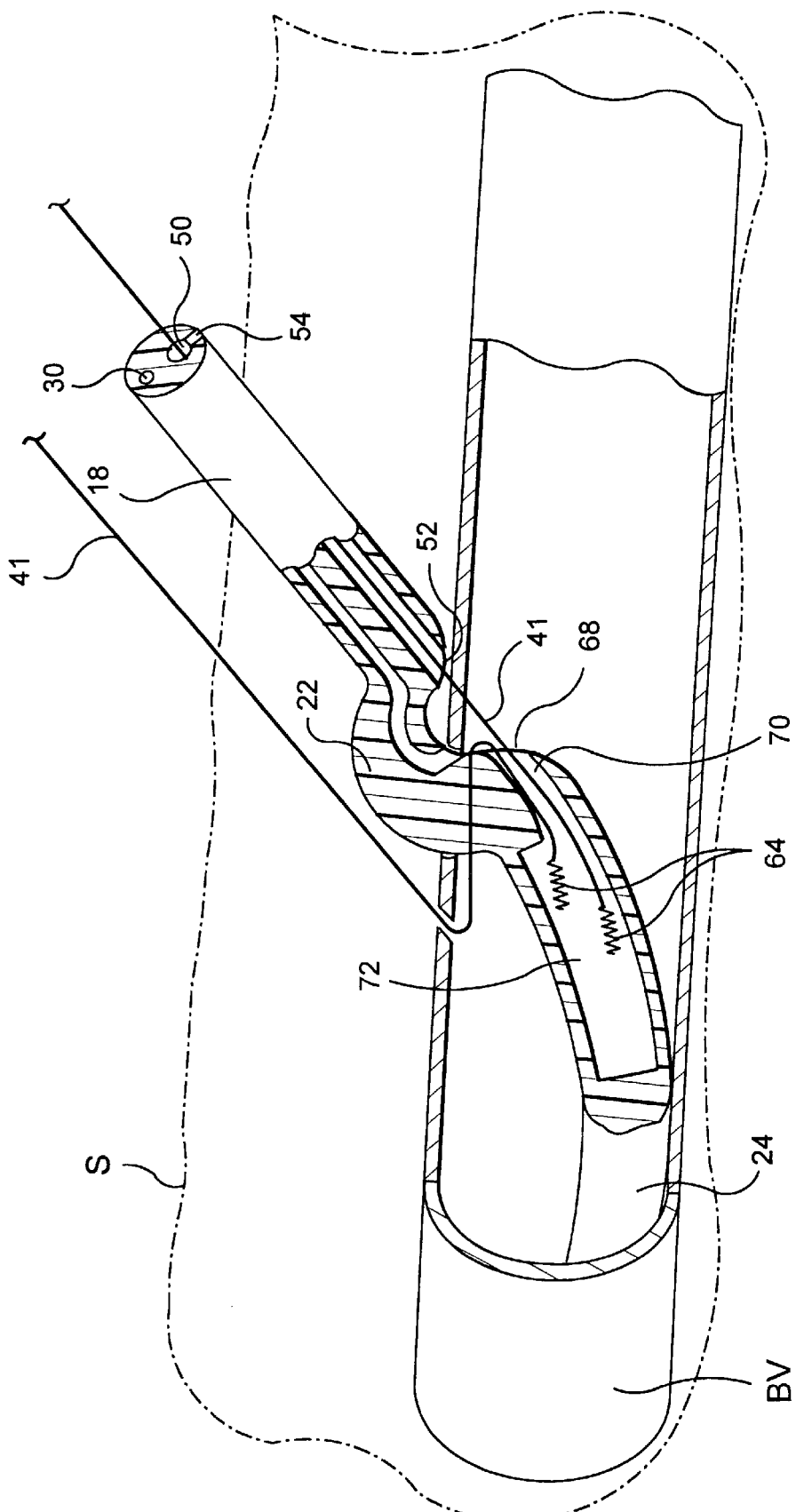
FIG. 17 shows a partially cross-sectional view of the blood vessel with a device according to the second embodiment of the present invention in a second desired position.

As shown in FIG. 17, the doctor then reorients the device 1' into the second desired position, as described above in regard to the first embodiment, the doctor presses upon gripping the surface 58 to urge the sharp, distal end of the puncture needle 56 distally out of the opening 52, through the wall of the blood vessel and into the opening 56 so that the opening 61 is within the suture retention chamber 72. Thereafter, the doctor inserts the plunger 66 into the central channel 59 and pushes it forward to release the anchor member 64 and the second suture 41 into the suture retention chamber 72. Those skilled in the art will understand that, instead of inserting a second suture 41 at this point, a gripping device may be introduced through the central channel 59 into the suture retention chamber 72 to grab and retrieve the anchor member 64 and draw it out through the central channel 59. This allows for the formation of a suture loop 41' without the need to knot two separate strands of suture 41 together.

Figure 18:
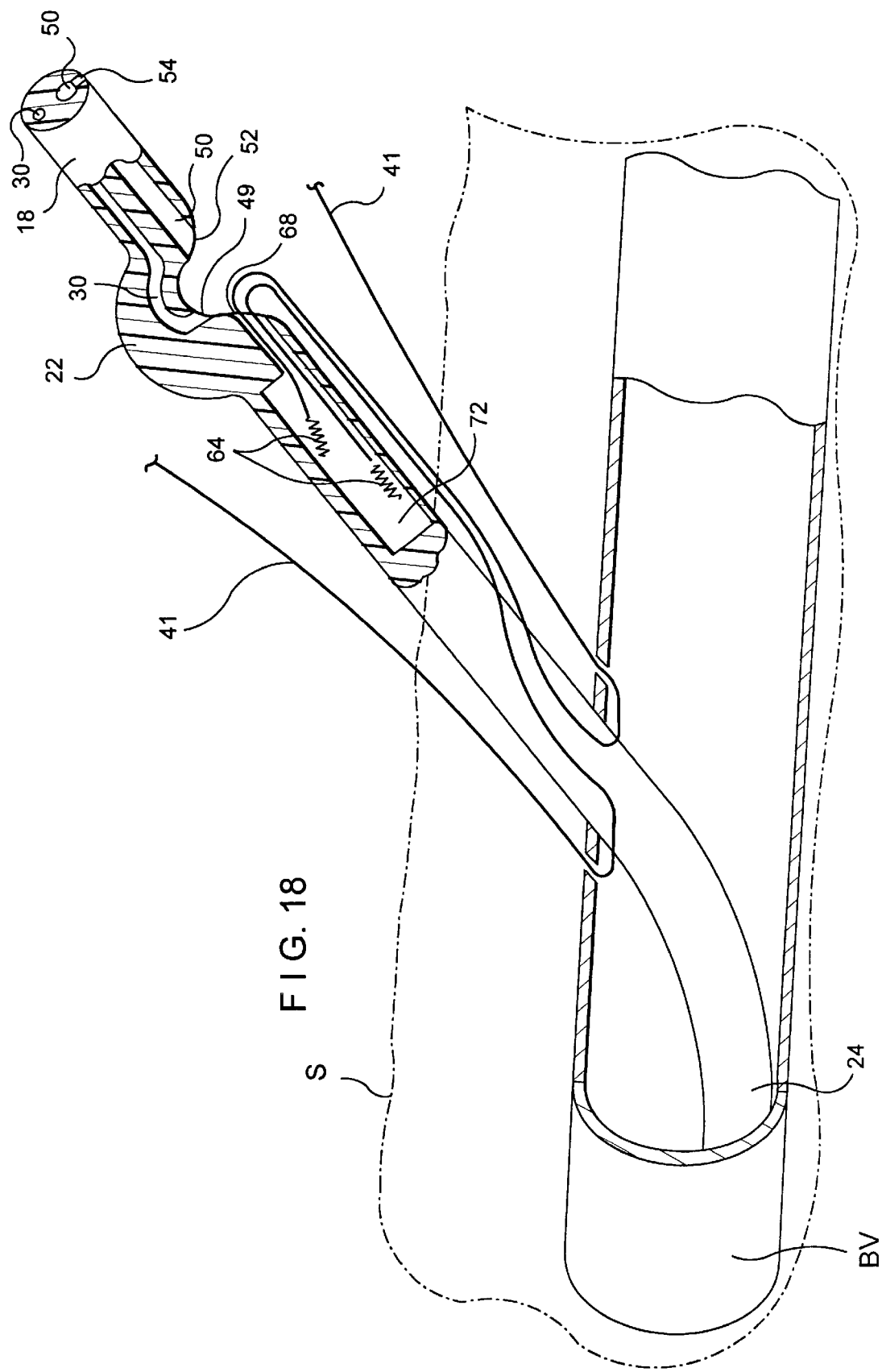
FIG. 18 shows a partially cross-sectional view of the blood vessel wherein the device according to the second embodiment has been partially withdrawn from the blood vessel.
Figure 19:
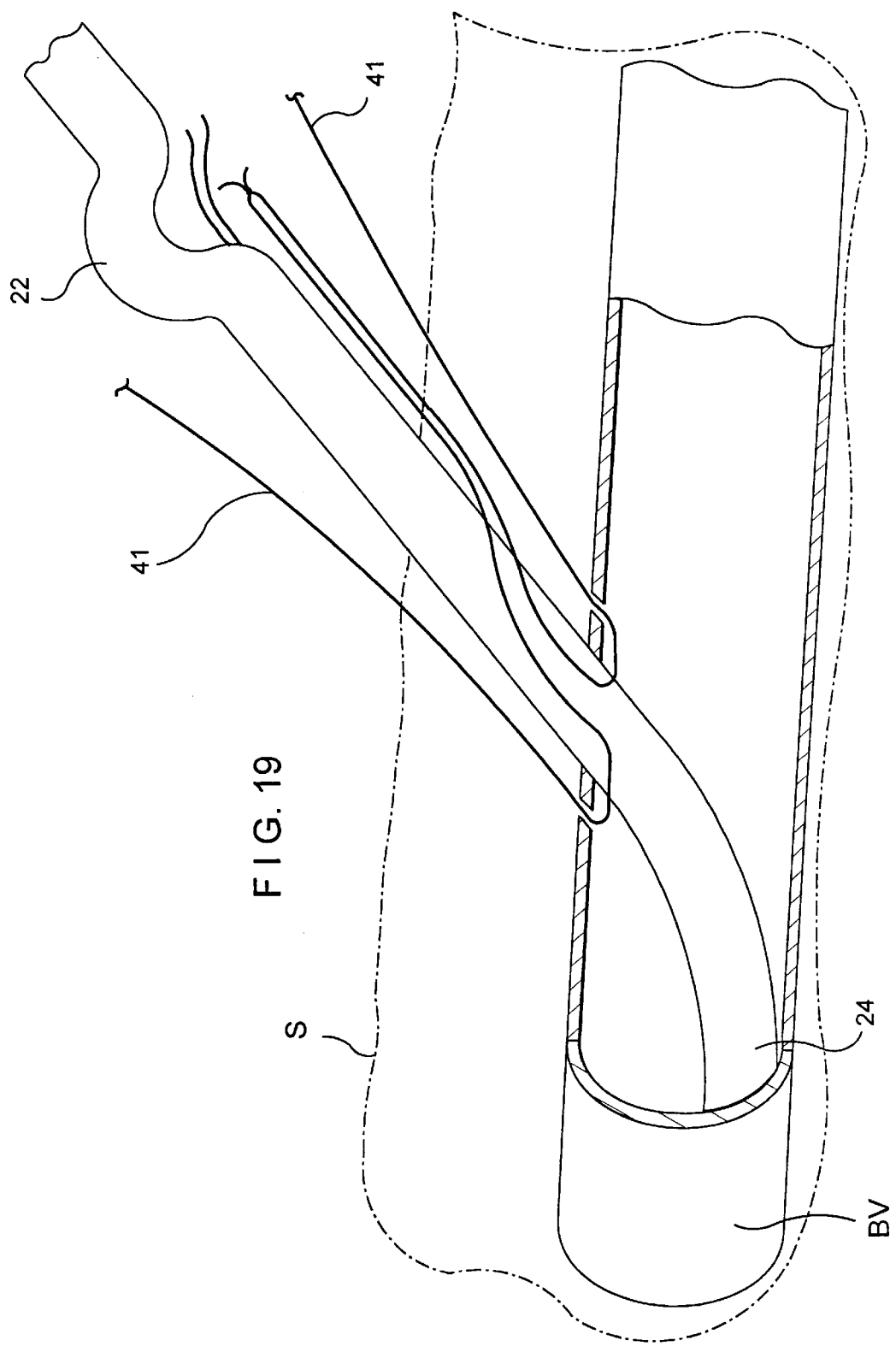
FIG. 19 shows a partially cross-sectional view of the blood vessel wherein the sutures have been severed from the anchor members and tied together.

The doctor then withdraws the device 1' from the body, as shown in FIG. 18, so that the ends of the sutures 41 extending from the opening 68 may be cut to release the sutures from the anchor members 64. Then, as shown in FIG. 19, these ends of the sutures 41 are tied together and the other ends are knotted together and tightened to seal the puncture.

Those skilled in the art will understand that, for larger punctures, the device 1' may be used to insert as many sutures 41 as are required to seal the puncture. Specifically, in order to close punctures larger than size 9.0 French, a single suture 41 may not be sufficient. Therefore, instead of using the device 1' as described above to insert two sutures 41 approximately 180° apart, a doctor may, for example, insert four sutures 41 at 90° intervals using the technique described above. Then, when the device 1' has been withdrawn from the body, the doctor must knot together a first pair of sutures 41 which are separated by approximately 180° and then knot the second pair. The two pairs of sutures 41 may be distinguished by color coding or any similar technique.

Figure 20:
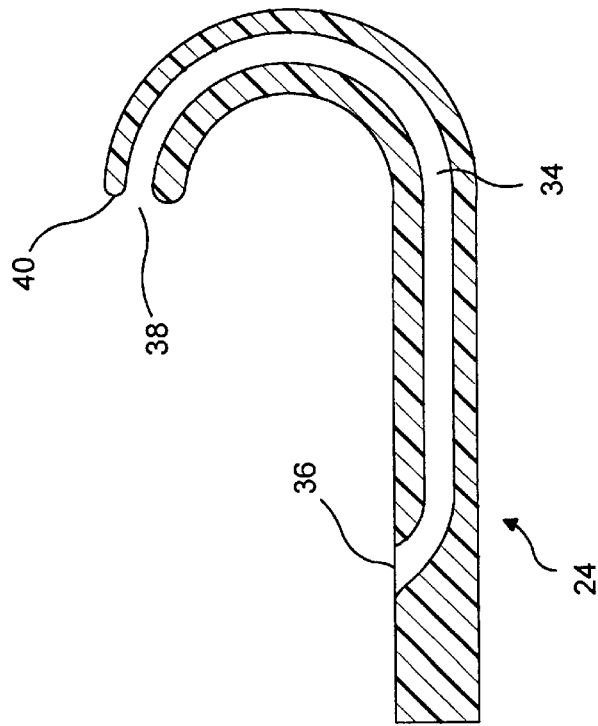
FIG. 20 shows a side view of a cross-section of a distal portion of a suturing device according to a third embodiment of the present invention.

A device 1" according to a third embodiment of the present invention is shown in FIG. 20. Aside from a modified distal part 24 as described below, the construction and operation of the device 1" may be identical to either of the first and second embodiments.

Specifically, the distal part 24 of the device 1" is constructed so that it has enhanced flexibility relative to the proximal part 18. In addition, the distal part 24 is biased so that, when in an unstressed state, it is "J" shaped—that is, the distal part 24 is curved so that the distal opening 38 formed in the second end 40 faces proximally. This facilitates insertion of the device 1" so that it contacts an inner wall of the blood vessel without damaging it. Specifically, the flexibility and "J" shape of the second end 40 allows the second end 40 to deflect away from the blood vessel's lining without penetrating or damaging the lining thereof. Of course, when received on the guide wire 44, the "J" shape of the distal part 24 will be less pronounced. However, the bias will maintain a slight curvature of the second end 40 deflecting the impact of the device 1" from the inside lining of the blood vessel.

Figure 21:
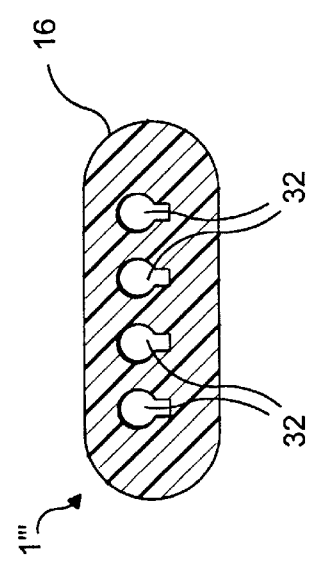
FIG. 21 shows a cross-section of a distal portion of a device according to the fourth embodiment of the invention.

As described above, in order to close punctures larger than size 9.0 French, a single suture 41 may not be sufficient. Thus, as shown in FIG. 21, a device 1''' according to a fourth embodiment of the invention may receive four needles 37 arranged side-by-side in four needle retention bores 32 formed in a flexible tube 16 of substantially oval cross-section. Other than the oval cross-section and the provision of four needles, the construction and operation of the device 1''' is similar to that of the device 1 according to the first embodiment.

The oval cross section increases the stiffness of the device 1''' in the plane in which the four needles lie side-by-side, while retaining flexibility to bend perpendicularly to that plane. The four needles 37 of the device 1''' are coupled together in pairs and each pair of needles will be positioned so that the needles 37 of each pair penetrate the wall of the blood vessel on opposite sides of the puncture (approximately 180° apart). When the device 1''' has been removed from the body, each pair is then knotted together and the two knots are tightened to seal the puncture.

Of course, those skilled in the art will understand that each of the variations of the device 1 according to the first embodiment may also be applied to the device 1'''. Similarly, those skilled in the art will recognize that four needles 37 may be received in a device 1''' having two needle retention bores 32, each being of a length sufficient to hold two needles 37 arranged in series end-to-end.

Rather than sealing the puncture by tying a knot in the suture 41 and pushing the knot to the puncture, a sealing device 100 may be employed to pull the edges of puncture together using the suture 41 and applying adhesive to seal the site. Several embodiments of a sealing device according to the present invention are shown, for example, in FIGS. 22–27.

Figure 22:
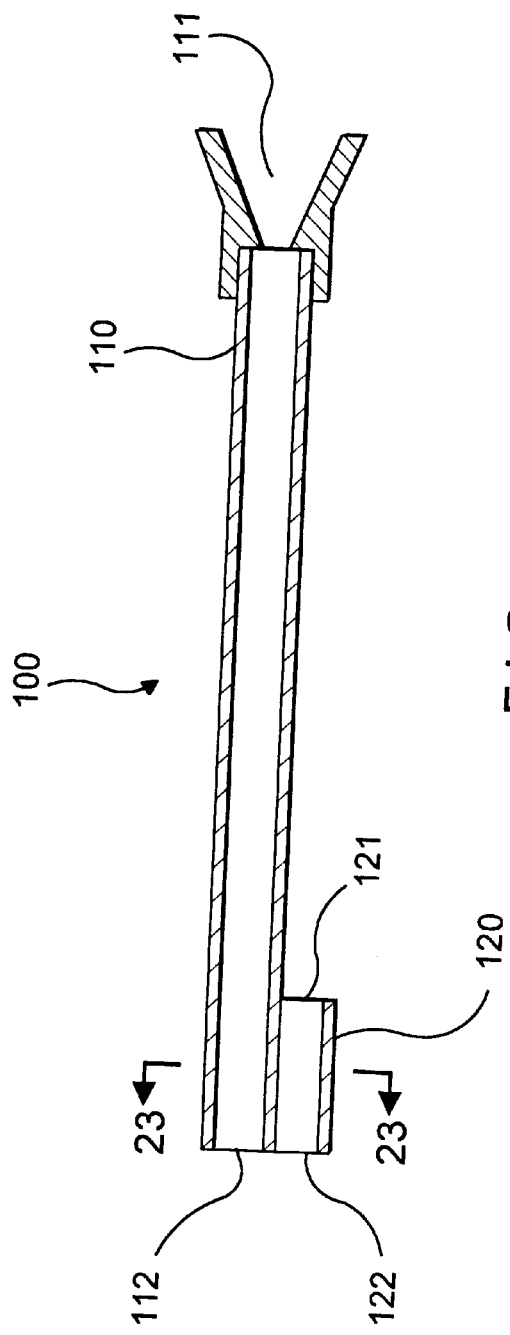
FIG. 22 shows a side view a fifth embodiment of a sealing device according to the present invention.
Figure 23:
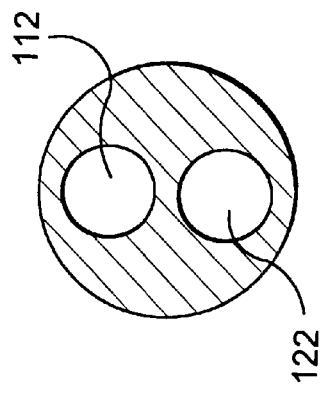
FIG. 23 shows a cross-sectional view of the sealing device of FIG. 22.

FIGS. 22 and 23 show one embodiment of such a sealing device 100. In this embodiment, the sealing device 100 is shaped as an elongated member having, for example, an adhesive channel 110 and a suture channel 120 running substantially parallel to one another and connected along one edge. The adhesive channel 110 extends from a proximal opening 111 to a distal opening 112, with the proximal opening 111 adapted, for example, for connection to an adhesive source (not shown). The suture channel 120 may be relatively short compared to the adhesive channel 110, with the adhesive channel having a length of, for example 20.0 to 100.0 millimeters and the suture channel having a length of, for example, 5 to 50 millimeters. The suture channel 120 extends from a proximal opening 121 to a distal opening 122. The distal opening 122 of the suture channel 120, and hence the diameter of the suture channel itself, may be relatively small, for example between 0.5 and 2.0 millimeters.

Figure 24:
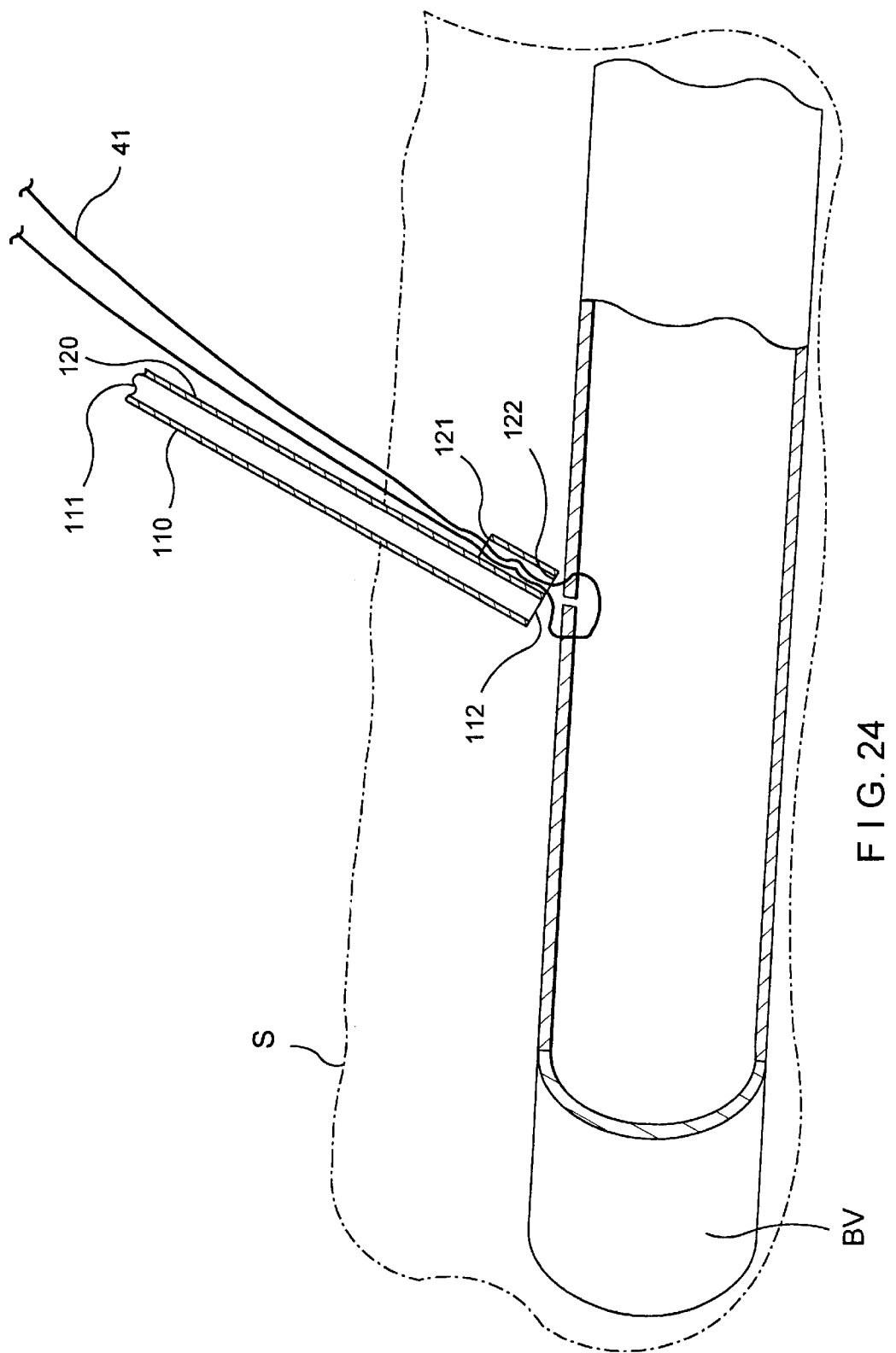
FIG. 24 shows a side view of the sealing device of FIG. 22 in use near a blood vessel.

As shown in FIG. 24, after the suture 41 has been drawn through the wall of the blood vessel and detached from the stitching device 1 the suture 41 may be drawn through the suture channel 120 from the distal opening 122 to the proximal opening 121. The relatively short length of the suture channel 120 facilitates the passing of the suture 41 through the suture channel 120. It will be understood that as the suture 41 is drawn through the suture channel 120 via the distal opening 122, thereby drawing in any slack in the suture 41, the puncture in the blood vessel will be pulled shut by the suture 41. At this point, adhesive (not shown) may be forced through the adhesive channel 110 and onto and around the closed puncture, thereby sealing the puncture. The adhesive may be, for example, a plasma-derived adhesive, collagen-based adhesive, cyanoacrylate adhesive, or any other suitable adhesive. After the puncture has been sealed, the suture 41 may, for example, be withdrawn from the puncture or left in place in the puncture.

Figure 25:
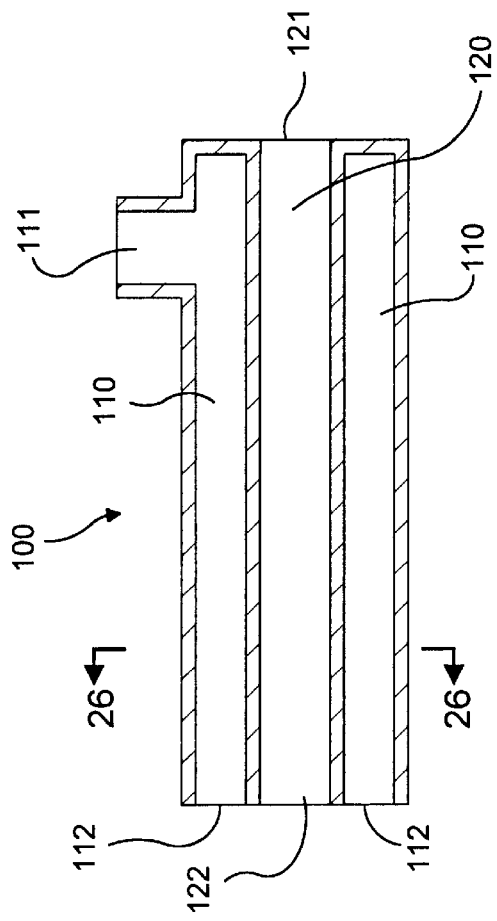
FIG. 25 shows a side of a sixth embodiment of a sealing device according to the present invention.
Figure 26:
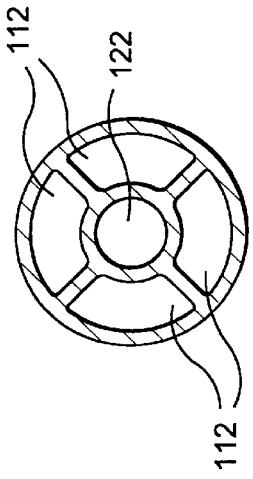
FIG. 26 shows a cross-sectional view of the sealing device of FIG. 25.

FIGS. 25 and 26 show an alternative embodiment of a sealing device 100 according to the present invention. In this embodiment, the sealing device 100 includes a series of adhesive channels 110. The adhesive channels 110 are each in fluid relationship to a single proximal opening 111, and each fluid channel 110 extends, for example, to a respective one of a series of distal openings 112. The proximal opening 111 may be adapted for connection to an adhesive source (not shown). In this manner, the adhesive (not shown) may pass from the proximal opening 111, through the adhesive channels 110, and out the distal openings 112.

As can be seen from FIG. 26, the adhesive channels 110 may preferably be substantially arcuate in cross-section. The adhesive channels 110 surround a suture channel 120, and as a group have a generally annular cross-section and are generally co-axial with the suture channel 120, as shown for example in FIG. 26. The suture channel 120 is, for example, co-axial with the sealing device as a whole. The suture channel 120 may preferably have a diameter between, for example, 0.5 and 2.0 millimeters. The suture channel and the adhesive channels (and hence the sealing device as a whole) may preferably have a length between, for example, 20.0 and 100.0 millimeters.

The manner of using this embodiment of the sealing device 100 is similar to that of using the above-described embodiment. After the suture 41 has been drawn through the wall of the blood vessel and detached from the stitching device 1, the suture 41 may be drawn through the suture channel 120 from the distal opening 122 to the proximal opening 121. As the suture 41 is drawn through the suture channel 120 via the distal opening 122, thereby drawing in any slack in the suture 41, the puncture in the blood vessel will be pulled shut by the suture 41. At this point, adhesive (not shown) may be forced through the adhesive channel 110 and onto and around the closed puncture, thereby sealing the puncture. The adhesive may be, for example, a plasma-derived adhesive, collagen-based adhesive, cyanoacrylate adhesive, or any other suitable adhesive. The plurality of adhesive channels 110 surrounding the suture channel 120 ensures an adequate distribution of the adhesive around the puncture. After the puncture has been sealed, the suture 41 may be withdrawn, for example, from the puncture or left in place.

Figure 27:
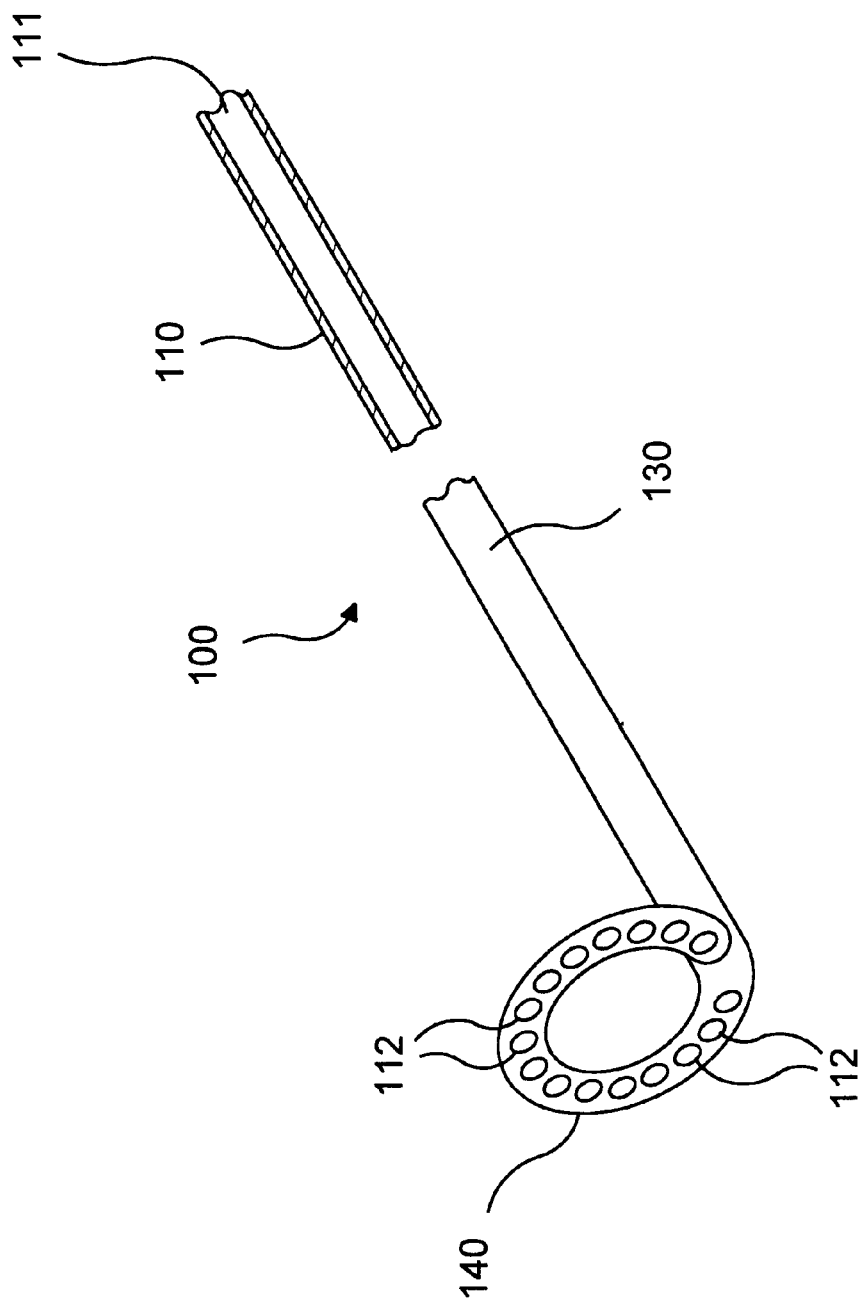
FIG. 27 shows a perspective view of a seventh embodiment of a sealing device according to the present invention, in use near an anatomical structure.

FIG. 27 shows a third embodiment of a sealing device 100 according to the present invention. In this embodiment, the sealing device 100 includes an elongated tube 130 that is bent, for example, into a loop 140 at one end. The tube 130 has an adhesive channel 110 extending therethrough from a proximal opening 111 to, for example, a plurality of distal openings 112 disposed on the loop 140. Alternatively, the elongated tube 130 and the loop 140 may be formed separately and then connected so that an adhesive channel 110 in the elongated tube 130 and an adhesive channel in the loop 140 are in fluid connection with one another. In this manner, adhesive (not shown) may enter the adhesive channel 110 via the proximal opening 111 in the elongated tube 130, pass through the adhesive channel 110, and exit the adhesive channel 110 via the plurality of distal openings 112 located on the loop 140. The internal diameter of the loop may be relatively small, for example between 0.5 and 2.0 millimeters.

After the suture 41 has been drawn through the vessel and detached from the stitching device 1, the suture 41 may be passed through the loop 140. It can be understood that as the suture 41 is drawn through the loop 140, thereby taking up any slack in the suture 41, the puncture in the blood vessel will be pulled shut by the suture 41. At this point the adhesive may be applied via the adhesive channel 110 and the distal openings 112. The adhesive may be, for example, a plasma-derived adhesive, collagen-based adhesive, cyanoacrylate adhesive, or any other suitable adhesive. The plurality of distal openings 112 and their arrangement along the loop 140 ensures an adequate distribution of adhesive around the puncture. Various shapes of the loop 140 and arrangements of the distal openings 112 may be suited to a variety of puncture shapes and sizes.

The sealing device of the present invention described above may be employed in conjunction with any stitching device capable of placing sutures 41 around openings or punctures in anatomical structures. The stitching device described above, however, is particularly advantageous in conjunction with the sealing device of the present invention because of its effectiveness an minimal cross-section. Once the sutures 41 have been pulled through the anatomical structure, the sutures 41 may be separated from the stitching device and then used with the sealing device of the present invention.

There are many variations of the above described embodiments which will be apparent to those skilled in the art. It is understood that these modifications are within the teaching of the present invention which is to be limited only by the claims appended hereto. In addition, although the operation of the various embodiments has been described in regard to the sealing of an opening in the wall of a blood vessel, those skilled in the art will understand that this invention may also be used to seal openings in various internal organs and structures.

What is claimed is:

1. A sealing device for sealing an opening in an anatomical structure within a living body comprising an elongated member including a suture channel extending axially therethrough from a suture channel distal end to a suture channel proximal end and an adhesive channel extending axially therethrough from an adhesive channel distal end to an adhesive channel proximal end, wherein the suture channel distal end is separated from the suture channel proximal end by a distance substantially equal to a distance from the suture channel proximal end to the adhesive channel distal end, wherein the suture channel distal end and the adhesive channel distal end are located relative to one another so that, when a suture applied to seal the opening is drawn into the suture channel via the suture channel distal end, adhesive exiting the adhesive channel distal end will contact a portion of the anatomical structure adjacent to the opening.

2. The sealing device according to claim 1, wherein a length of the suture channel is shorter than a length of the adhesive channel.

3. The sealing device according to claim 2, wherein a length of the suture channel is between 5.0 and 50.0 millimeters and wherein a length of the adhesive channel is between 20.0 and 100.0 millimeters.

4. The sealing device according to claim 1, wherein the suture channel and the adhesive channel are each substantially circular in cross-section.

5. The sealing device according to claim 4, wherein a diameter of the suture channel is between 0.5 and 2.0 millimeters and wherein a diameter of the adhesive channel is between 0.5 and 4.0 millimeters.

6. The sealing device according to claim 5, wherein a length of the suture channel is between 5.0 and 50.0 millimeters and wherein a length of the adhesive channel is between 20.0 and 100.0 millimeters.

7. The sealing device according to claim 1, wherein the at least one adhesive channel includes a plurality of adhesive channels.

8. The sealing device according to claim 7, wherein the suture channel has a substantially circular cross section, wherein the suture channel is axially centered on an axial centerline of the elongated member, wherein each of the plurality of adhesive channels is substantially arcuate in cross section, and wherein the plurality of adhesive channels are, as a group, substantially annular in cross-section.

9. The sealing device according to claim 8, wherein a length of the suture channel and each of the plurality of adhesive channels is between 20.0 and 100.0 millimeters.

10. The sealing device according to claim 8, wherein a diameter of the suture channel is between 0.5 and 2.0 millimeters and a diameter of the elongated member is between 2.0 and 6.0 millimeters.

11. The sealing device according to claim 10, wherein a length of the suture channel and each of the plurality of adhesive channels is between 20.0 and 100.0 millimeters.

12. A device for sealing an opening in an anatomical structure within a living body, comprising:
   an elongated tubular member extending from a distal end to a proximal end thereof, wherein a fluid channel extends through the elongated tubular member from a proximal opening to the distal end; and
   a tubular loop connected to the distal end of the elongated tubular member, the tubular loop including a central fluid channel in fluid connection with the elongated tubular member fluid channel, and wherein the tubular loop is oriented in a plane substantially perpendicular to a longitudinal axis of the elongated tubular member, a distal face of the tubular loop having a plurality of holes therein for communicating the tubular loop fluid channel with an outside of the tubular loop.

13. The device according to claim 12, wherein the inner diameter of the tubular loop is between 0.5 and 2.0 millimeters.

14. A method for sealing an opening in anatomical structure, comprising the steps of:
   passing a length of suture through the anatomical structure so that the length of suture spans the opening inside the anatomical structure and exits the anatomical structure on opposite sides of the opening;
   introducing a sealing device to a position proximate to the opening, wherein the sealing device includes a suture channel extending between a suture channel proximal end and a suture channel distal end and an adhesive channel extending between an adhesive channel proximal end and an adhesive channel distal end;
   passing the ends of the length of suture through the suture channel;
   pulling the ends of the suture channel to draw the length of suture through the suture channel to close the opening;
   applying adhesive to the opening through the adhesive channel of the sealing device to seal the opening.

15. The method according to claim 14, further comprising the step of pulling on one of the pair of ends of the length of suture to remove the length of suture from the anatomical structure.

16. The method according to claim 14, wherein the step of passing a length of suture through the anatomical structure includes the steps of:
   guiding a stitching device into an opening in an anatomical structure, wherein the stitching device includes:
      a proximal part and a distal part coupled together by a curved central part, wherein a gap is formed between proximal and distal parts by the curved central part; and
      a needle retention channel having a plurality of needles received therein, the needle retention channel extending through the distal part to an opening formed in the proximal end of the distal part facing the gap, wherein the length of suture is coupled between the distal ends of first and second needles;
   positioning the stitching device so that the curved central part is within the opening with the needle retention channel opening on a distal side of the anatomical structure and a needle receiving channel opening on a proximal side of the anatomical structure;
   drawing on one of a first portion of the length of suture and a pull cord attached to a distal end of a first needle to draw the first needle proximally out of the needle retention channel so that the first needle and the corresponding end of the first portion of the length of suture pass through the anatomical structure and into a needle receiving channel extending from an opening formed in a distal end of the proximal part through the proximal part;
   rotating the stitching device to a second desired position so that a second part of the anatomical structure adjacent to the opening is located within the gap;
   drawing on one of a second portion of the length of suture and a pull cord attached to a distal end of a second needle to draw the second needle and the corresponding end of the second portion of the length of suture proximally out of the needle retention channel, through the anatomical structure and into the needle receiving channel;
   withdrawing the first and second needles from the needle receiving channel to draw the ends of the length of suture out of the body; and
   detaching the ends of the length of suture from the first and second needles.

17. The method according to claim 16, further comprising the step of pulling on one of the ends of the length of suture to remove the length of suture from the anatomical structure.

18. The method according to claim 16, wherein the stitching device further includes a flash back lumen extending from a proximal end of the stitching device to the needle retention channel, and wherein, for procedures in which the anatomical structure is a blood vessel, observation of blood in the flash back lumen and not in the needle receiving channel provides a visual indication that the stitching device is in a desired position within the blood vessel.

19. The method according to claim 16, wherein the stitching device is inserted into the anatomical structure along a previously inserted guide wire.

20. The method according to claim 14, wherein the step of introducing the length of suture into the anatomical structure includes the steps of:
   guiding a stitching device into an opening in an anatomical structure, wherein the stitching device includes:
      a proximal part and a distal part coupled together by a curved central part so that a gap is formed between the proximal and distal parts;
      a puncture needle slidably received within a puncture needle channel extending through the proximal part to an opening formed in the distal end of the proximal part and a puncture needle receiving channel extending through the distal part to a suture retention channel; and
      a piston slidably received in a central lumen of the puncture needle;
   positioning the stitching device so that the curved central part is within the opening with the puncture needle channel opening on a proximal side of the anatomical structure and the puncture needle receiving channel opening on a distal side of the anatomical structure;
   pushing the puncture needle distally through the puncture needle channel, to penetrate the anatomical structure, enter the puncture needle receiving channel and pass into the suture retention chamber;
   moving the piston distally through the central channel to force an interior section of a first portion of suture having a first anchor member attached thereto out of the central channel and into the suture retention chamber;

withdrawing the puncture needle and the piston from the distal part and so that distal ends thereof are received within the proximal part;

rotating the stitching device to a second desired position so that a second part of the anatomical structure adjacent to the opening is located within the gap;

withdrawing the piston and inserting into the central channel an interior section of a second portion of suture having a second anchor member attached thereto;

moving the piston distally through the central channel to force the interior section of the second portion of suture out of the central channel and into the suture retention chamber;

withdrawing the stitching device from the body;

detaching the anchor members from the interior sections of the first and second portions of suture;

fastening together the interior sections of the first and second portions of suture to form the length of suture; and separating the length of suture from the stitching device to form the pair of ends of the length of suture.

21. The method according to claim 20, wherein the stitching device further includes a flash back lumen extending from a proximal end of the stitching device to the puncture needle receiving channel, and wherein, for procedures in which the anatomical structure is a blood vessel, when blood is observed in the flash back lumen and not in the puncture needle channel, the user determines that the device is in a desired position within the blood vessel.

22. A system for sealing an opening in anatomical structure, comprising:

a stitching device including:

a proximal part and a distal part coupled together by a curved central part so that a gap is formed between the proximal and distal parts; and a needle retention channel having a plurality of needles received therein, the needle retention channel extending through the distal part to an opening formed in the proximal end of the distal part facing the gap, wherein a length of suture is coupled between the distal ends of first and second needles; and a sealing device for applying adhesive to the opening, wherein the sealing device includes a suture channel extending therethrough from a suture channel distal end to a suture channel proximal end and an adhesive channel extending through an elongated member substantially parallel to the suture channel from an adhesive channel proximal end to an adhesive channel distal end, wherein the suture channel distal end and the adhesive channel distal end are substantially equidistant from the adhesive channel proximal end.

23. The system according to claim 22, wherein the suture channel has a substantially circular cross section and wherein the adhesive channel includes a plurality of substantially arcuate adhesive channels arranged substantially annularly about an axial centerline of the elongated member.

24. The system according to claim 23, wherein the sealing device includes a tubular loop coupled to a distal end of the elongated tubular member so that the tubular loop lies in a plane oriented substantially perpendicularly to the axial centerline of the elongated member, wherein an interior channel of the tubular loop extends from an input fluidly coupled to the adhesive channel to a plurality of holes extending through the surface of a distal face of the tubular loop, and wherein the suture channel extends through a central opening of the tubular loop.

\* \* \* \* \*